United States Patent
Suzuki et al.

(10) Patent No.: US 12,260,950 B2
(45) Date of Patent: Mar. 25, 2025

(54) NUTRIENT INTAKE AMOUNT ESTIMATION SYSTEM, NUTRIENT INTAKE AMOUNT ESTIMATION METHOD, NUTRIENT INTAKE AMOUNT ESTIMATION DEVICE, STORAGE MEDIUM, AND NUTRIENT INTAKE AMOUNT OUTPUT METHOD

(71) Applicant: TOTO LTD., Kitakyushu (JP)

(72) Inventors: Kenta Suzuki, Fukuoka (JP); Mizuki Watanabe, Fukuoka (JP); Isao Okayama, Fukuoka (JP); Yusuke Sato, Fukuoka (JP); Ryoji Nakamura, Fukuoka (JP)

(73) Assignee: TOTO LTD., Kitakyushu (JP)

( * ) Notice: Subject to any disclaimer, the term of this patent is extended or adjusted under 35 U.S.C. 154(b) by 839 days.

(21) Appl. No.: 17/206,470

(22) Filed: Mar. 19, 2021

(65) Prior Publication Data
US 2022/0093233 A1 Mar. 24, 2022

Related U.S. Application Data

(63) Continuation of application No. PCT/JP2020/036136, filed on Sep. 24, 2020.

(51) Int. Cl.
*B01L 3/00* (2006.01)
*A47L 15/42* (2006.01)
(Continued)

(52) U.S. Cl.
CPC ............. *G16H 20/60* (2018.01); *G16H 40/63* (2018.01); *A47L 15/4276* (2013.01); *Y10S 530/859* (2013.01)

(58) Field of Classification Search
CPC ........ G16H 20/60; G16H 40/63; G16H 40/67; G16H 50/20; A47L 15/4276; Y10S 530/859
See application file for complete search history.

(56) References Cited

U.S. PATENT DOCUMENTS

2017/0089875 A1* 3/2017 Hasegawa .......... A61B 10/0038
2017/0328884 A1 11/2017 Bezemer et al.

FOREIGN PATENT DOCUMENTS

| CN | 107003298 | 8/2017 |
|---|---|---|
| CN | 108511084 | 9/2018 |

(Continued)

OTHER PUBLICATIONS

International Search Report and Written Opinion for International Application No. PCT/JP2020/036136 mailed on Dec. 15, 2020, 7 pages.

*Primary Examiner* — Jennifer Wecker
*Assistant Examiner* — Oyeleye Alexander Alabi
(74) *Attorney, Agent, or Firm* — Amin, Turocy & Watson, LLP

(57) ABSTRACT

A nutrient intake amount estimation system according to an embodiment includes: a sensor that is disposed in a toilet space, and configured to detect an excretion smell related to excretion of a user of the toilet space; an estimation unit configured to estimate an estimated nutrient intake amount that is an amount of nutrients taken by the user by using an output of an estimation model that outputs information indicating an amount of nutrients estimated to be taken by the user in accordance with an input based on an output value of the sensor; and an output unit configured to output information based on the estimated nutrient intake amount.

15 Claims, 15 Drawing Sheets

(51) Int. Cl.

| | | |
|---|---|---|
| *A61L 27/16* | (2006.01) | |
| *A61L 27/56* | (2006.01) | |
| *B01F 23/00* | (2022.01) | |
| *B01F 23/41* | (2022.01) | |
| *B01F 101/23* | (2022.01) | |
| *B01L 7/00* | (2006.01) | |
| *B01L 9/00* | (2006.01) | |
| *B23Q 17/24* | (2006.01) | |
| *C07K 14/705* | (2006.01) | |
| *C08F 220/56* | (2006.01) | |
| *C08L 33/26* | (2006.01) | |
| *C12M 1/34* | (2006.01) | |
| *C12Q 1/04* | (2006.01) | |
| *C12Q 1/18* | (2006.01) | |
| *C12Q 1/6844* | (2018.01) | |
| *C12Q 1/686* | (2018.01) | |
| *G01N 1/31* | (2006.01) | |
| *G01N 21/17* | (2006.01) | |
| *G01N 21/3577* | (2014.01) | |
| *G01N 21/359* | (2014.01) | |
| *G01N 21/39* | (2006.01) | |
| *G01N 21/45* | (2006.01) | |
| *G01N 21/64* | (2006.01) | |
| *G01N 21/77* | (2006.01) | |
| *G01N 21/78* | (2006.01) | |
| *G01N 27/414* | (2006.01) | |
| *G01N 30/12* | (2006.01) | |
| *G01N 30/68* | (2006.01) | |
| *G01N 30/70* | (2006.01) | |
| *G01N 30/72* | (2006.01) | |
| *G01N 30/88* | (2006.01) | |
| *G01N 33/00* | (2006.01) | |
| *G01N 33/18* | (2006.01) | |
| *G01N 33/50* | (2006.01) | |
| *G01N 33/53* | (2006.01) | |
| *G01N 33/543* | (2006.01) | |
| *G01N 33/68* | (2006.01) | |
| *G01N 33/74* | (2006.01) | |
| *G01N 35/00* | (2006.01) | |
| *G01N 35/04* | (2006.01) | |
| *G01N 35/10* | (2006.01) | |
| *G06T 7/00* | (2017.01) | |
| *G06T 7/90* | (2017.01) | |
| *G16H 20/60* | (2018.01) | |
| *G16H 40/63* | (2018.01) | |
| *H10K 10/46* | (2023.01) | |
| *H10K 85/00* | (2023.01) | |
| *H10K 85/20* | (2023.01) | |

(56) References Cited

FOREIGN PATENT DOCUMENTS

| | | | |
|---|---|---|---|
| CN | 109935301 | 6/2019 | |
| CN | 110506211 | 11/2019 | |
| CN | 111305338 | 6/2020 | |
| CN | 111395480 | 7/2020 | |
| CN | 111599462 | 8/2020 | |
| EP | 1949852 | 7/2008 | |
| JP | 07-274849 | 10/1995 | |
| JP | 2003-162584 | 6/2003 | |
| JP | 2010-197081 | 9/2010 | |
| JP | 2017-067538 | 4/2017 | |
| JP | 2019-074328 | 5/2019 | |
| JP | 2019074328 A * | 5/2019 | ............... E03D 9/08 |
| TW | 201112179 | 4/2011 | |
| WO | WO-2013086372 A1 * | 6/2013 | ......... G01G 19/4146 |

* cited by examiner

| NUTRIENT INTAKE TARGET BALANCE ID | NAME | NUTRIENT RATIO | | | ... |
| --- | --- | --- | --- | --- | --- |
| | | CARBO-HYDRATES | FAT | PROTEIN | |
| TB1 | Modern Standard | 60 | 25 | 15 | ... |
| TB2 | Athlete Diet | 35 | 25 | 40 | ... |
| TB3 | Paleo Diet | 40 | 45 | 15 | ... |
| TB4 | Vegetarian Diet | 65 | 20 | 15 | ... |
| TB5 | Low-carb Diet | 30 | 40 | 30 | ... |
| TB6 | Elderly Diet | 65 | 20 | 15 | ... |
| ... | ... | ... | ... | ... | ... |

FIG.6

| MODEL ID | TYPE | MODEL DATA | ... |
|---|---|---|---|
| M1 | NEURAL NETWORK | MDT1 | ... |
| M2 | SUPPORT VECTOR MACHINE | MDT2 | ... |
| M3 | RANDOM FOREST | MDT3 | ... |
| M4 | LOGISTIC REGRESSION | MDT4 | ... |
| M5 | DECISION JUNGLE | MDT5 | ... |
| M6 | PERCEPTRON | MDT6 | ... |
| M7 | BAYESIAN DISCRIMINATION | MDT7 | ... |
| M8 | k-NEAREST NEIGHBOR ALGORITHM | MDT8 | ... |
| M9 | HIDDEN MARKOV MODEL | MDT9 | ... |
| ... | ... | ... | ... |

| USER ID | ATTRIBUTE INFORMATION | NUTRIENT INTAKE TARGET BALANCE | ... |
|---------|----------------------|-------------------------------|-----|
| U1 | ATB1 | TB1 | ... |
| U2 | ATB2 | TB5 | ... |
| U3 | ATB3 | TB3 | ... |
| ... | ... | ... | ... |

NUTRIENT INTAKE AMOUNT ESTIMATION SYSTEM, NUTRIENT INTAKE AMOUNT ESTIMATION METHOD, NUTRIENT INTAKE AMOUNT ESTIMATION DEVICE, STORAGE MEDIUM, AND NUTRIENT INTAKE AMOUNT OUTPUT METHOD

CROSS-REFERENCE TO RELATED APPLICATION

This application is a Continuation application of International Application PCT/JP2020/036136, filed on Sep. 24, 2020, and designating the U.S., the entire contents of which are incorporated herein by reference.

FIELD

An embodiment disclosed herein relates to a nutrient intake amount estimation system, a nutrient intake amount estimation method, a nutrient intake amount estimation device, a storage medium, and a nutrient intake amount output method.

BACKGROUND

In recent years, health consciousness has been developed, and demand has been increasing for checking a state of health and improving a life as needed by monitoring (observing) the state of health every day. It can be said that excrement excreted from a human body is an important vital sign indicating a state of health of a person, and there has been developed a technique of determining dietary content and the like of a person who excreted the excrement by using information such as a smell (evacuation gas) generated from the excrement (for example, Patent Literatures 1 and 2).

A relation between the evacuation gas generated from the excrement and a meal that has been taken is becoming clear nowadays. For example, in a case of taking a well-balanced meal, the evacuation gas contains short-chain fatty acids (an acetic acid, a propionic acid, a butyric acid). In a case of taking excessive carbohydrates (saccharides), the evacuation gas contains a lactic acid, a succinic acid, a formic acid, or a branched fatty acid (an isobutyric acid, isovaleric acid). In a case of taking excessive protein, the evacuation gas contains ammonia, phenol, or hydrogen sulfide. Additionally, in a case of taking excessive fat, the evacuation gas contains hydrogen sulfide, amines, a bile acid, or an acidic gas derived from steatorrhea.

CITATION LIST

Patent Literature

Patent Literature 1: Japanese Patent Application Laid-open No. 2019-74328
Patent Literature 2: Japanese Patent Application Laid-open No. H7-274849

SUMMARY

Technical Problem

However, with the system as described above, a load on a user of a toilet space cannot be necessarily suppressed, the load for observing nutrients taken by the user of the toilet space.

For example, in Patent Literature 1, image information of food and drink and bar code information written on a label, that is, information other than information related to excretion of the user of the toilet space is required. Accordingly, the system is complicated, and the load on the user of the toilet space is increased. In Patent Literature 2, information about food eaten by a person (user of the toilet space) is required, that is, information other than the information related to excretion of the user of the toilet space is similarly required. In this way, in Patent Literatures 1 and 2, the load on a person (user of the toilet space) as an observation target for nutrients is large, and it is not highly convenient. Thus, there has been a demand for enabling nutrients taken by the user of the toilet space to be observed without applying a load on the user of the toilet space.

In view of the situation as described above, an object of the present invention is to suppress the load on the user of the toilet space for observing nutrients taken by the user of the toilet space.

The embodiment disclosed herein provides a nutrient intake amount estimation system, a nutrient intake amount estimation method, a nutrient intake amount estimation device, a storage medium, and a nutrient intake amount output method capable of suppressing the load on the user of the toilet space for observing nutrients taken by the user of the toilet space.

Solution to Problem

A nutrient intake amount estimation system according to an aspect of the embodiment, comprising: a sensor that is disposed in a toilet space, and configured to detect an excretion smell related to excretion of a user of the toilet space; an estimation unit configured to estimate an estimated nutrient intake amount that is an amount of nutrients taken by the user by using an output of an estimation model that outputs information indicating an amount of nutrients estimated to be taken by the user in accordance with an input based on an output value of the sensor; and an output unit configured to output information based on the estimated nutrient intake amount.

The nutrient intake amount estimation system according to an aspect of the embodiment estimates the amount of nutrients taken by the user of the toilet space by using the estimation model and the output value of the sensor disposed in the toilet space without using information such as a meal taken by the user of the toilet space. Due to this, the nutrient intake amount estimation system can suppress the load on the user of the toilet space for observing nutrients taken by the user of the toilet space. Accordingly, the user of the toilet space or a person who manages nutrients taken by the user (hereinafter, also referred to as "user and the like") refers to information based on an estimated nutrient intake amount that has been output, and the user and the like can grasp inclination of meals taken by the user for improving nutrients to be taken.

The nutrient intake amount estimation system according to an aspect of the embodiment, further comprising: a storage unit configured to store a target nutrient intake amount that is a nutrient intake amount aimed at by the user, wherein the output unit outputs the target nutrient intake amount and the estimated nutrient intake amount.

The nutrient intake amount estimation system according to an aspect of the embodiment can enable the user and the like to recognize the relation between the target nutrients and nutrients under the present situation by outputting both of the information based on the target nutrient amount and the information based on the nutrient amount under the present situation. For example, the nutrient intake amount estimation system can visualize the relation between the target nutrient amount and the nutrient amount under the present situation by displaying both of the target nutrient amount and the nutrient amount under the present situation. Due to this, the user and the like can compare the target nutrient intake of the user with an actual nutrient intake thereof, and grasp a difference between the target nutrient intake and the actual nutrient intake for improving nutrients to be taken.

The nutrient intake amount estimation system according to an aspect of the embodiment, further comprising: a storage unit configured to store a target nutrient intake amount that is a nutrient intake amount aimed at by the user, wherein the output unit outputs a difference between the target nutrient intake amount and the estimated nutrient intake amount.

The nutrient intake amount estimation system according to an aspect of the embodiment can cause the user and the like to grasp the difference between the actual nutrient intake and the target nutrient intake for improving nutrients to be taken by outputting the difference between the target nutrient intake amount aimed at by the user and the estimated nutrient intake amount.

In the nutrient intake amount estimation system according to an aspect of the embodiment, wherein the output unit displays recommendation information based on a difference between the target nutrient intake amount and the estimated nutrient intake amount.

The nutrient intake amount estimation system according to an aspect of the embodiment can cause the user and the like to grasp how to improve nutrients to be taken based on the recommendation information for improving nutrients to be taken by displaying the recommendation information based on the difference between the target nutrient intake amount aimed at by the user and the estimated nutrient intake amount.

In the nutrient intake amount estimation system according to an aspect of the embodiment, wherein the target nutrient intake amount stored in the storage unit is set based on selection by the user or information related to the user.

With the nutrient intake amount estimation system according to an aspect of the embodiment, the user and the like of the toilet space can set an appropriate target value corresponding to the situation of the user. In this way, the nutrient intake amount estimation system can suppress the load on the user of the toilet space for observing nutrients taken by the user of the toilet space.

In the nutrient intake amount estimation system according to an aspect of the embodiment, wherein the estimation unit estimates an estimated nutrient intake balance that is a balance of nutrients taken by the user as the estimated nutrient intake amount; and the output unit outputs information based on the estimated nutrient intake balance.

With the nutrient intake amount estimation system according to an aspect of the embodiment, the user and the like can grasp inclination of meals taken by the user by referring to the output estimated nutrient intake balance for improving the nutrient intake balance.

In the nutrient intake amount estimation system according to an aspect of the embodiment, wherein the estimation unit estimates an estimated specific nutrient intake amount that is an amount of a specific nutrient taken by the user as the estimated nutrient intake amount; and the output unit outputs information based on the estimated specific nutrient intake amount.

With the nutrient intake amount estimation system according to an aspect of the embodiment, the user and the like can grasp an intake state of the amount of the specific nutrient for improving intake related to the amount of the specific nutrient by referring to the information based on the estimated specific nutrient intake amount of the amount of the specific nutrient that has been output.

In the nutrient intake amount estimation system according to an aspect of the embodiment, wherein the output unit displays a balance of at least two nutrients selected from carbohydrates, fat, protein, vitamins, and minerals as a graph.

The nutrient intake amount estimation system according to an aspect of the embodiment can visually present the nutrient balance to the user and the like by displaying the balance of nutrients as a graph. For example, the nutrient intake amount estimation system can focus on at least two nutrients, and can visually display the nutrient balance. Due to this, the user and the like can grasp the nutrient balance intuitively.

In the nutrient intake amount estimation system according to an aspect of the embodiment, wherein the sensor is disposed on a toilet seat or a closet bowl in the toilet space.

The nutrient intake amount estimation system according to an aspect of the embodiment can improve detection accuracy by being disposed at a place where an excretion smell such as an evacuation gas can be easily detected.

In the nutrient intake amount estimation system according to an aspect of the embodiment, wherein the estimation unit is connected to the output unit in a communicable manner via an electric communication line, and information is transmitted from the estimation unit to the output unit via the electric communication line.

With the nutrient intake amount estimation system according to an aspect of the embodiment, the estimation unit such as the nutrient intake amount estimation device and the output unit such as a user terminal can be optionally disposed, and a flexible system configuration can be implemented.

The nutrient intake amount estimation system according to an aspect of the embodiment, further comprising: an authentication unit configured to authenticate the user.

The nutrient intake amount estimation system according to an aspect of the embodiment enables individual information to be protected by personal authentication. The nutrient intake amount estimation system can manage the collected excretion smell and the user who generated the excretion smell in association with each other by authenticating the user of the toilet space.

The nutrient intake amount estimation system according to an aspect of the embodiment, further comprising: a transmission unit configured to transmit data of the estimated nutrient intake amount to a terminal device via an electric communication line.

The nutrient intake amount estimation system according to an aspect of the embodiment can display the information on a more conspicuous place, or transmit the information to an informant required for health care.

In the nutrient intake amount estimation system according to an aspect of the embodiment, the excretion smell contains a smell of at least one of feces, urine, and gas excreted by the user.

The nutrient intake amount estimation system according to an aspect of the embodiment can estimate the nutrient intake amount of the user by using various smells of feces, urine, gas, and the like excreted by the user.

A nutrient intake amount estimation method according to an aspect of the embodiment, comprising: a detection step of detecting an excretion smell related to excretion of a user of a toilet space by a sensor disposed in the toilet space; an estimation step of estimating an estimated nutrient intake amount that is an amount of nutrients taken by the user by using an output of an estimation model that outputs information indicating an amount of nutrients estimated to be taken by the user in accordance with an input based on an output value of the sensor; and an output step of outputting information based on the estimated nutrient intake amount.

In the nutrient intake amount estimation method according to an aspect of the embodiment, the amount of nutrients taken by the user of the toilet space is estimated by using the estimation model and the output value of the sensor disposed in the toilet space without using information such as a meal taken by the user of the toilet space. Due to this, the nutrient intake amount estimation method can suppress the load on the user of the toilet space for observing nutrients taken by the user of the toilet space. The user and the like of the toilet space can grasp inclination of meals taken by the user for improving nutrients to be taken by referring to the output information based on the estimated nutrient intake amount.

A nutrient intake amount estimation device according to an aspect of the embodiment, comprising: an acquisition part configured to acquire an output value that is output by a sensor disposed in a toilet space after detecting an excretion smell related to excretion of a user of the toilet space; and an estimation part configured to estimate an estimated nutrient intake amount that is an amount of nutrients taken by the user by using an output of an estimation model that outputs information indicating an amount of nutrients estimated to be taken by the user in accordance with an input based on the output value of the sensor.

The nutrient intake amount estimation device according to an aspect of the embodiment estimates the amount of nutrients taken by the user of the toilet space by using the estimation model and the output value of the sensor disposed in the toilet space without using information such as a meal taken by the user of the toilet space. Due to this, the nutrient intake amount estimation device can suppress the load on the user of the toilet space for observing nutrients taken by the user of the toilet space. The nutrient intake amount estimation device provides the information based on the estimated nutrient intake amount that has been estimated to the user and the like of the toilet space to enable the user and the like to grasp inclination of meals taken by the user for improving nutrients to be taken.

A computer-readable storage medium according to an aspect of the embodiment, in which a computer program is non-transitorily recorded, the computer program being used for: acquiring information based on a nutrient intake amount of a user that is estimated by using an output of an estimation model that outputs information indicating an amount of nutrients estimated to be taken by the user, and information based on a target nutrient intake amount that is a nutrient intake amount aimed at by the user in accordance with an input based on an output value that is output by a sensor disposed in a toilet space after detecting an excretion smell related to excretion of the user of the toilet space; and outputting the information based on the target nutrient intake amount together with the information based on the nutrient intake amount.

The storage medium according to an aspect of the embodiment can enable the user to easily compare the target nutrient intake amount of himself/herself with the actual nutrient intake amount by outputting the information based on the nutrient intake amount aimed at by the user of the toilet space together with the information based on the estimated nutrient intake amount of the user by the recorded computer program (output program). In this way, the storage medium can suppress the load on the user of the toilet space for observing nutrients taken by the user of the toilet space.

Advantageous Effects of Invention

According to an aspect of the embodiment, it is possible to suppress the load on the user of the toilet space for observing nutrients taken by the user of the toilet space.

BRIEF DESCRIPTION OF DRAWINGS

FIG. 5 is a diagram illustrating an example of a nutrient intake target balance information storage part according to the embodiment.

FIG. 6 is a diagram illustrating an example of a model information storage part according to the embodiment.

DESCRIPTION OF EMBODIMENTS

The following describes an embodiment of a nutrient intake amount estimation system disclosed herein in detail with reference to the attached drawings. The present invention is not limited to the embodiment described below.

1. Nutrient Intake Amount Estimation Processing

Figure 1:
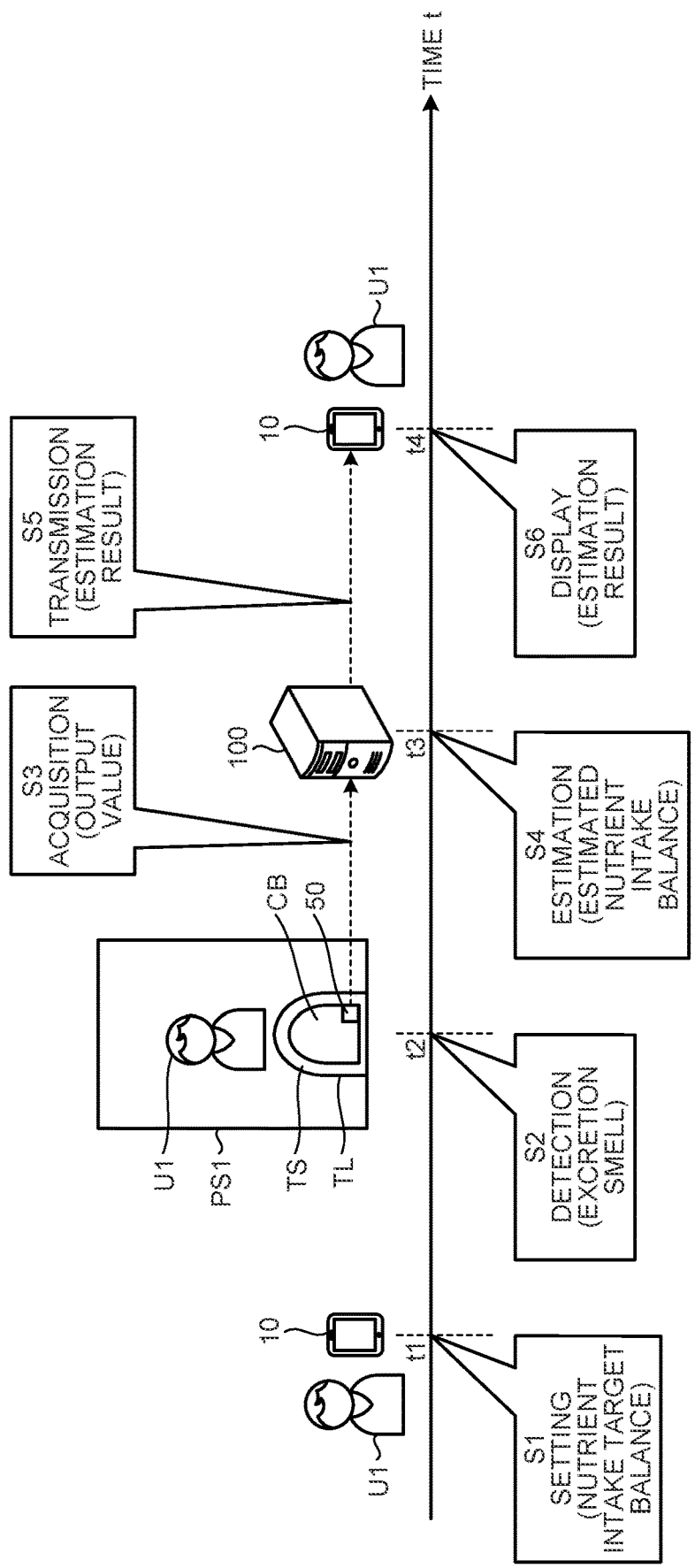
FIG. 1 is a diagram illustrating an example of nutrient intake amount estimation processing according to an embodiment.

First, the following describes an outline of information processing performed by a nutrient intake amount estimation system 1 according to the embodiment (refer to FIG. 3) with reference to FIG. 1. FIG. 1 is a diagram illustrating an example of the nutrient intake amount estimation processing according to the embodiment. In the following description, a balance of nutrients taken by a person (also referred to as a "nutrient intake balance") is exemplified as an example of an estimated amount of nutrient intake (estimated nutrient intake amount), but the estimated nutrient intake amount may also be an intake amount of each nutrient. In the following description, a balance of three nutrients including carbohydrates, fat, and protein is exemplified as an example of the nutrient intake balance, but other nutrients such as vitamins and minerals may be included therein.

FIG. 1 illustrates a schematic plan view of a toilet space PS1 in which a toilet device (hereinafter, referred to as a "toilet TL") is disposed while exemplifying the toilet space PS1 as a toilet of a household (house) as an example of the toilet space. FIG. 1 exemplifies a case in which a sensor device 50 is disposed on a toilet seat TS of the toilet TL, the sensor device 50 functioning as a smell sensor that detects an excretion smell containing a smell of at least one of feces, urine, and gas.

In FIG. 1, a user U1 is exemplified as a user of the toilet space PS1, and a user terminal 10 used by the user U1 is exemplified as a nutrient intake amount output device. The nutrient intake amount output device is not limited to the user terminal 10, but this point will be described later.

First, in the example of FIG. 1, at a date and time t1, the user U1 sets a nutrient intake balance aimed at by the user U1 (also referred to as a "nutrient intake target balance") by using the user terminal 10 (Step S1). An application for monitoring the nutrient intake balance (also referred to as a "nutrient balance monitoring application") is installed in the user terminal 10, and the user U1 sets the nutrient intake target balance by the nutrient balance monitoring application. For example, the user U1 operates the user terminal 10 to set "Modern Standard" (refer to FIG. 5) as the nutrient intake target balance. The user terminal 10 transmits information indicating the set nutrient intake target balance of the user U1 to a nutrient intake amount estimation device 100. The nutrient intake target balance of the user U1 is not necessarily set by the user U1 himself/herself, but may be automatically set based on attribute information and the like of the user U1.

At a date and time t2, the user U1 performs an excretion action in the toilet space PS1 in which the sensor device 50 is disposed, and the sensor device 50 detects an excretion smell of the user U1 (Step S2). The sensor device 50 then transmits an output value corresponding to detection of the excretion smell of the user U1 to the nutrient intake amount estimation device 100. Due to this, the nutrient intake amount estimation device 100 acquires the output value of the sensor device 50 corresponding to the excretion smell of the user U1 (Step S3). The nutrient intake amount estimation system 1 may specify a person who has used the toilet space PS1 at the date and time t2 as the user U1 (personal authentication) by using the user terminal 10 or another device, but this point will be described later. For example, in the example of FIG. 1, personal authentication is performed by using a device that is disposed in the toilet space PS1 for receiving various operations related to the toilet performed by the user (also referred to as a "toilet operation device"). For example, the toilet operation device may be a remote control for changing strength or a position for hip washing by a warm water washing toilet seat. In the following description, it is assumed that the user U1 operates the toilet operation device, and the nutrient intake amount estimation device 100 receives, from the toilet operation device, information indicating that a person who has used the toilet space PS1 at the date and time t2 is the user U1.

At a date and time t3, the nutrient intake amount estimation device 100 estimates a balance of nutrients taken by the user U1 (also referred to as an "estimated nutrient intake balance") by using the output value of the sensor device 50 corresponding to the excretion smell of the user U1 (Step S4). For example, the nutrient intake amount estimation device 100 estimates the estimated nutrient intake balance of the user U1 by using an output of a model that outputs information indicating a balance of nutrients estimated to be taken by the user (also referred to as an "estimation model") in accordance with an input based on the output value of the sensor. The nutrient intake amount estimation device 100 performs processing by using a model selected from among models M1 to M9 (refer to FIG. 6) as estimation models. The following describes a case in which the nutrient intake amount estimation device 100 performs processing by using the three models M1 to M3, but the models to be used are not limited to the three models described above, the models to be used are not limited to the models M1 to M3 but may be the other models M4 to M9, and the number of models are not limited to three. For example, the nutrient intake amount estimation device 100 estimates which of four balances including "well-balanced", "excessive in carbohydrates", "excessive in fat", and "excessive in protein" corresponds to the estimated nutrient intake balance of the user by using output results of the models M1 to M3. For example, the models M1 to M3 are classifiers for outputting, in accordance with the input based on the output value of the sensor device 50 that has detected the excretion smell, which of the four balances including "well-balanced", "excessive in carbohydrates", "excessive in fat", and "excessive in protein" corresponds to nutrients taken by the user corresponding to the excretion smell. The four classifications of "well-balanced", "excessive in carbohydrates", "excessive in fat", and "excessive in protein" are merely an example for explaining the classifier, and the classifier may be a classifier that outputs a larger number of classifications than the four classifications. For example, by using a classifier that outputs five or more classifications, the nutrient intake amount estimation device 100 may estimate which of the five or more classifications corresponds to the nutrients taken by the user. For example, the classifier may be a classifier that also outputs a classification related to a deficiency of each nutrient. In this case, there may be seven classifications including "well-balanced", "excessive in carbohydrates and deficient in fat", "excessive in carbohydrates and deficient in protein", "excessive in fat and deficient in carbohydrates", "excessive in fat and deficient in protein", "excessive in protein and deficient in carbohydrates", and "excessive in protein and deficient in fat". By using a classifier that outputs such seven classifications, the nutrient intake amount estimation device 100 can also estimate a deficiency similarly to an excess of each nutrient intake amount. As described above, the classifier may output an excess and a deficiency like the seven classifications described above.

That is, the nutrient intake amount estimation device 100 can estimate various classifications in accordance with an output of the classifier.

In the example of FIG. 1, the nutrient intake amount estimation device 100 estimates that the estimated nutrient intake balance of the user U1 is a nutrient balance "excessive in protein". For example, the nutrient intake amount estimation device 100 inputs, to the model M1, an input value generated by using the output value of the sensor device 50, and estimates that the estimated nutrient intake balance of the user U1 is the nutrient balance "excessive in protein" in a case in which an output result of the model M1 is information indicating "excessive in protein". The nutrient intake amount estimation device 100 generates an input value for the estimation model such as the model M1 by using the output value of the sensor device 50. The input value generated by using the output value of the sensor device 50 may be the output value of the sensor device 50 as it is, may be part of the output value of the sensor device 50, may be a value calculated from the output value of the sensor device 50, or the like. Details about estimation processing such as processing using output results of the models M1 to M3 will be described later.

The nutrient intake amount estimation device 100 transmits an estimation result to the user terminal 10 (Step S5). The nutrient intake amount estimation device 100 transmits, to the user terminal 10, information about the estimation result indicating that the estimated nutrient intake balance of the user U1 is "excessive in protein". For example, the nutrient intake amount estimation device 100 transmits, to the user terminal 10, information about a target setting indicating "Modern Standard" that is the nutrient intake target balance set by the user U1.

At a date and time t4, the user terminal 10 displays the estimation result (Step S6). The user terminal 10 displays the estimation result indicating that the estimated nutrient intake balance of the user U1 is "excessive in protein". For example, the user terminal 10 displays the estimation result indicating that the estimated nutrient intake balance of the user U1 is "excessive in protein" together with the target setting indicating the nutrient intake target balance set by the user U1.

In this way, the nutrient intake amount estimation system 1 estimates the nutrient intake balance of the user of the toilet space based on the estimation model and the detection result obtained by the sensor device 50 disposed in the toilet space. Due to this, the nutrient intake amount estimation system 1 can suppress a load on an estimation target person for the nutrient balance such as the user of the toilet space, and can observe the balance of nutrients taken by the user of the toilet space. As described above, with the nutrient intake amount estimation system 1, the user of the toilet space can obtain information about the nutrient balance by only performing a daily excretion action. Thus, convenience is especially high in a case in which the user of the toilet space continuously and daily uses a service related to estimation of the nutrient balance performed by the nutrient intake amount estimation system 1. That is, the nutrient intake amount estimation system 1 can suppress a load such as work that is performed by the user of the nutrient intake amount estimation system 1 such as the user of the toilet space to observe the balance of nutrients taken by the user of the toilet space. The user terminal 10 may display character information indicating the estimated nutrient intake balance of the user U1 or the nutrient intake target balance set by the user U1, or may display a diagram such as a graph (statistical chart) indicating the estimated nutrient intake balance of the user U1 or the nutrient intake target balance set by the user U1.

2. Display Example of Nutrient Intake Balance

Figure 2:
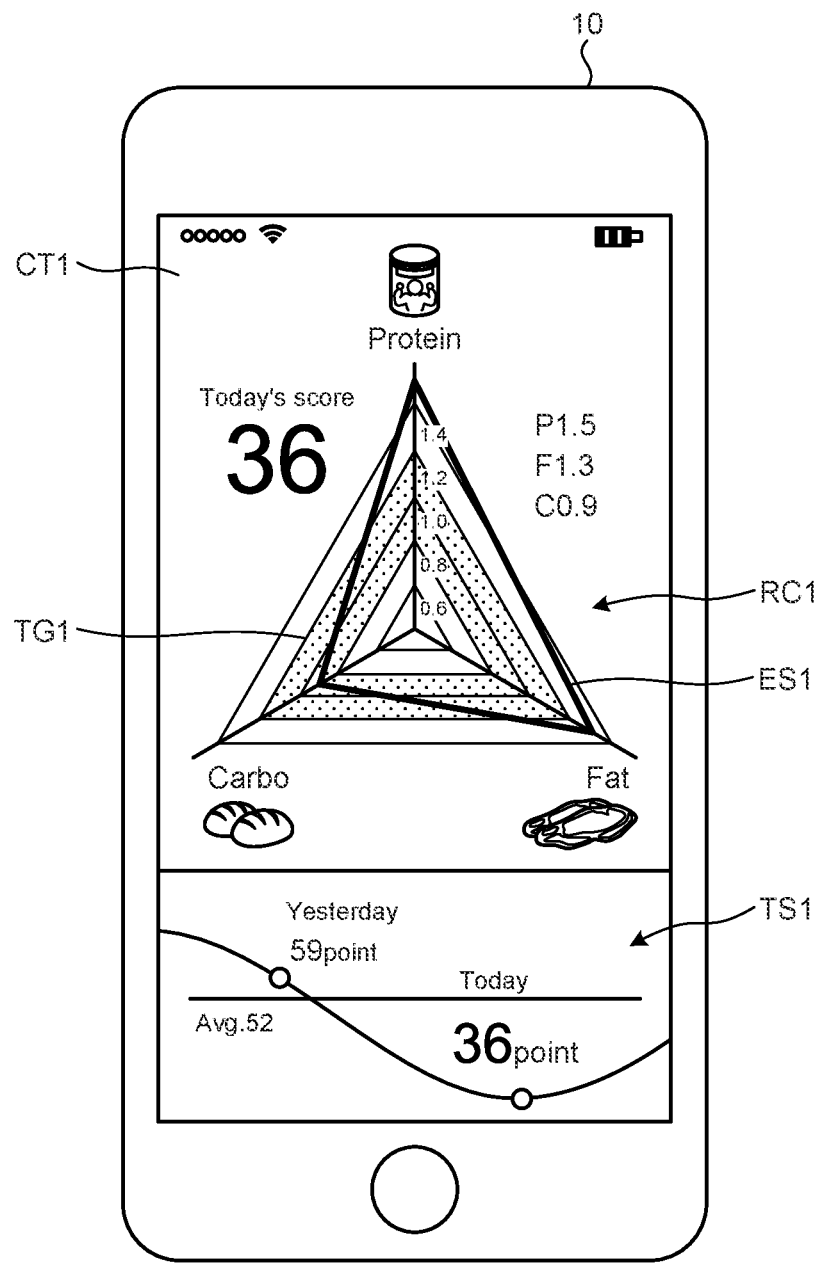
FIG. 2 is a diagram illustrating a display example of a nutrient intake amount output device.

The following describes a display example of the nutrient intake balance with reference to FIG. 2. FIG. 2 is a diagram illustrating a display example of the nutrient intake amount output device. Specifically, FIG. 2 illustrates a case in which the user terminal 10 serving as the nutrient intake amount output device displays a radar chart representing the estimated nutrient intake balance of the user U1 and the nutrient intake target balance set by the user U1. The radar chart is merely an example of a graph representing the nutrient intake target balance, and may be a graph in different format. Details about this point will be described later. The following exemplifies a case in which the user U1 in FIG. 1 is assumed to be a user of the toilet space PS1.

The nutrient intake amount estimation device 100 generates content CT1 including the information indicating "Modern Standard" that is the nutrient intake target balance of the user U1 and the information indicating the estimated nutrient intake balance of the user U1 that indicates "excessive in protein". The nutrient intake amount estimation device 100 generates the content CT1 including a radar chart RC1 in which an estimation chart ES1 corresponding to the estimated nutrient intake balance of the user U1 is superimposed on a target chart TG1 corresponding to the nutrient intake target balance of the user U1. The radar chart RC1 of the content CT1 includes the target chart TG1, the estimation chart ES1, and information indicating three axes thereof (carbohydrates, fat, and protein).

The nutrient intake amount estimation device 100 transmits the content CT1 to the user terminal 10, and the user terminal 10 displays the received content CT1. The content CT1 illustrated in FIG. 2 represents a display mode in a case of displaying various additional pieces of information, but the content CT1 does not necessarily include items other than the radar chart RC1.

In the example of FIG. 2, the target chart TG1 indicating the nutrient intake target balance corresponds to a hatched region, and ranges from 1.2 to 0.8. For example, the target chart TG1 indicates that a portion of 1.0 of each nutrient corresponds to a target value of the nutrient intake target balance, and a range from −20% to +20% is a range achieving a goal.

Herein, as "Modern Standard", an ideal balance of nutrient ratio is carbohydrates of "60%", fat of "25%", and protein of "15%" (refer to FIG. 5). Thus, for example, in "Modern Standard", a target value of carbohydrates is "60%", so that 1.0 on an axis that is oriented obliquely downward to the left represented as "Carbo" corresponds to a case in which the ratio of carbohydrates is "60%". In "Modern Standard", a target value of fat is "25%", so that 1.0 on an axis that is oriented obliquely downward to the right represented as "Fat" corresponds to a case in which the ratio of fat is "25%". In "Modern Standard", a target value of protein is "15%", so that 1.0 on an axis that is oriented upward represented as "Protein" corresponds to a case in which the ratio of protein is "15%".

The nutrient intake amount estimation device 100 generates the radar chart RC1 including the target chart TG1 having the range from 1.2 to 0.8 while a position corresponding to the target value of each nutrient in "Modern Standard" is assumed to be 1. The above description is merely an example, and the axes of the radar chart RC1 and divisions thereon may be appropriately changed. For example, the divisions on the axes of the radar chart RC1 may represent the ratio "%".

In the example of FIG. 2, the estimation chart ES1 representing the estimated nutrient intake balance passes through positions of estimation values corresponding to ratios of respective nutrients. For example, the estimation chart ES1 indicates that the estimation value of carbohydrates is 0.9, the estimation value of fat is 1.3, and the estimation value of protein is 1.5. The estimation chart ES1 indicates that protein has been excessively taken as compared with the target ratio.

The estimation chart ES1 is generated based on information estimated by the nutrient intake amount estimation device 100. For example, in a case in which the nutrient intake amount estimation device 100 estimates only the classification of the estimated nutrient intake balance of the user, the nutrient intake amount estimation device 100 may use an estimation chart corresponding to each classification of the nutrient balance. In this case, the nutrient intake amount estimation device 100 may store, as information for a chart, an estimation chart or a value of each nutrient in association with each classification of the nutrient balance, and generate the estimation chart ES1 by using this information for a chart.

For example, in a case in which the nutrient intake amount estimation device 100 estimates the ratio of each nutrient taken by the user, the nutrient intake amount estimation device 100 may generate the estimation chart by using the estimated ratio of each nutrient.

As illustrated in FIG. 2, the nutrient intake amount estimation device 100 may generate the content CT1 including estimation values of respective nutrients as character information. The nutrient intake amount estimation device 100 may also generate the content CT1 including a score related to the nutrient balance. For example, the nutrient intake amount estimation device 100 may calculate the score based on the nutrient intake target balance and the estimated nutrient intake balance. For example, the nutrient intake amount estimation device 100 may calculate the score to be higher as the estimated nutrient intake balance comes closer to the nutrient intake target balance. In the example of FIG. 2, the nutrient intake amount estimation device 100 calculates, to be 36, the score on a day when the content CT1 is generated. The nutrient intake amount estimation device 100 may generate the content CT1 including a history TS1 indicating a change of the score. The history TS1 indicates that the score on a previous day is 59, for example, indicates that the estimated nutrient intake balance on the previous day is closer to the nutrient intake target balance than the estimated nutrient intake balance on the day when the content CT1 is generated.

3. Configuration of Nutrient Intake Amount Estimation System

Figure 3:
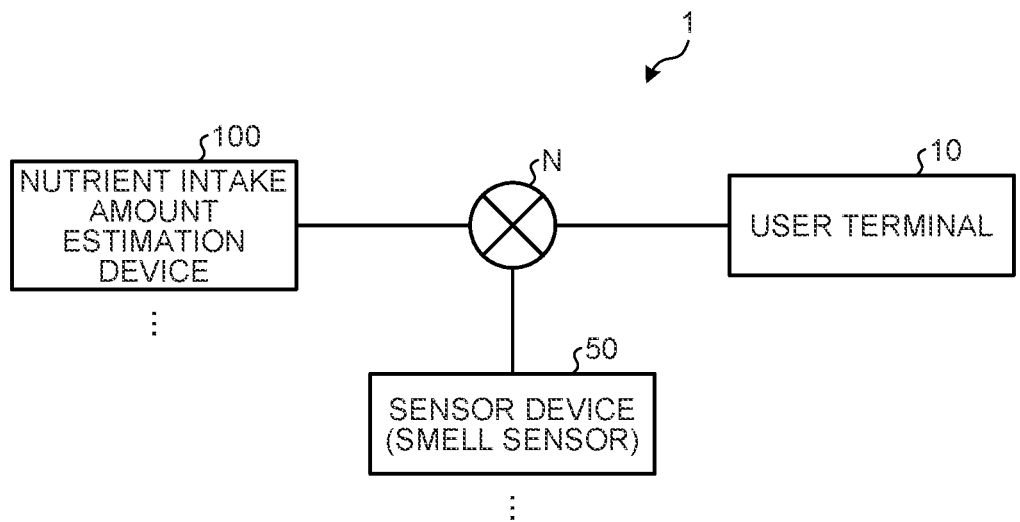
FIG. 3 is a diagram illustrating a configuration example of a nutrient intake amount estimation system according to the embodiment.

Next, the following describes a configuration of the nutrient intake amount estimation system 1 with reference to FIG. 3. FIG. 3 is a diagram illustrating a configuration example of the nutrient intake amount estimation system according to the embodiment. Specifically, FIG. 3 illustrates the configuration of the nutrient intake amount estimation system 1. The nutrient intake amount estimation system 1 includes the nutrient intake amount estimation device 100, the sensor device 50, and the user terminal 10. The nutrient intake amount estimation system 1 may include a plurality of the nutrient intake amount estimation devices 100, a plurality of the sensor devices 50, or a plurality of the user terminals 10.

The nutrient intake amount estimation device 100 is an information processing device that inputs, to the estimation model, an input value generated by using the output value of the sensor device 50 that has detected the excretion smell, and estimates the estimated nutrient intake balance taken by the user by using an output of the estimation model. The nutrient intake amount estimation device 100 includes a database such as a storage part 120 (refer to FIG. 4), and performs nutrient intake amount estimation processing.

The nutrient intake amount estimation device 100 is connected to the sensor device 50 and the user terminal 10 to be able to communicate with each other in a wired or wireless manner via a predetermined network N such as the Internet. The nutrient intake amount estimation device 100 may be connected to the sensor device 50 and the user terminal 10 in any manner so long as information can be transmitted and received, may be connected thereto to be able to communicate with each other in a wired manner, or may be connected thereto to be able to communicate with each other in a wireless manner.

The sensor device 50 functions as a smell sensor that detects a smell. The sensor device 50 has a communication function implemented by a communication circuit and the like, and transmits information about a detected smell to the nutrient intake amount estimation device 100. The sensor device 50 is disposed in the toilet space PS1 to detect the excretion smell related to excretion of the user of the toilet space PS1. The sensor device 50 is disposed on a toilet seat or a closet bowl in the toilet space. The sensor device 50 is not necessarily disposed on the toilet seat or the closet bowl, but may be disposed at any position where the excretion smell can be detected in the toilet space. For example, the sensor device 50 may be disposed on a urinal in the toilet space.

FIG. 1 exemplifies a case in which the sensor device 50 is disposed on the toilet seat TS of the toilet TL, but the sensor device 50 may be disposed at any position in the toilet space PS1 so long as the excretion smell can be detected. For example, the sensor device 50 may be disposed at another position of the toilet TL such as a closet bowl CB of the toilet TL. As the sensor device 50, a part for detecting a smell (sensor) and a part having a communication function (a communication circuit and the like) may be separately disposed.

The sensor device 50 includes a sensor that detects an excretion smell. The sensor device 50 may include any type of sensor that can detect an excretion smell. For example, the sensor device 50 includes a sensor that converts a chemical phenomenon into an electric signal to be output. For example, the sensor device 50 includes a semiconductor type smell sensor (also referred to as a "semiconductor sensor"), or a crystal oscillator type smell sensor.

In the example of FIG. 1, the sensor device 50 includes the semiconductor sensor. The sensor device 50 outputs an output value in accordance with detection of a smell by the semiconductor sensor. For example, the output value of the sensor device 50 is an output voltage. The sensor device 50 may include a plurality of sensors having different sensitivities and may output a plurality of output values, but details about this point will be described later.

The user terminal 10 is an information processing device used by the user. The user terminal 10 is, for example, implemented by a smartphone, a mobile phone, a personal digital assistant (PDA), a tablet terminal, a notebook personal computer (PC), and the like. FIG. 1 exemplifies a case in which the user terminal 10 is a smartphone used by the user.

The user terminal 10 is a nutrient intake amount output device that outputs the nutrient intake target balance together with the nutrient intake balance. The user terminal 10 is connected to the nutrient intake amount estimation device 100 in a communicable manner via the Internet (the predetermined network N and the like), and transmits/receives information to/from the nutrient intake amount estimation device 100. The user terminal 10 receives content indicating the nutrient intake target balance and the nutrient intake balance from the nutrient intake amount estimation device 100, and displays the received content.

For example, the user terminal 10 may be connected to the toilet operation device in a communicable manner by using a predetermined wireless communication function such as Bluetooth (registered trademark) or Wireless Fidelity (Wi-Fi) (registered trademark).

4. Functional Configuration of Each Device

The following specifically describes functional configurations of the nutrient intake amount estimation device 100 and the user terminal 10 as an example of the nutrient intake amount output device.

4-1. Functional Configuration of Nutrient Intake Amount Estimation Device

Figure 4:
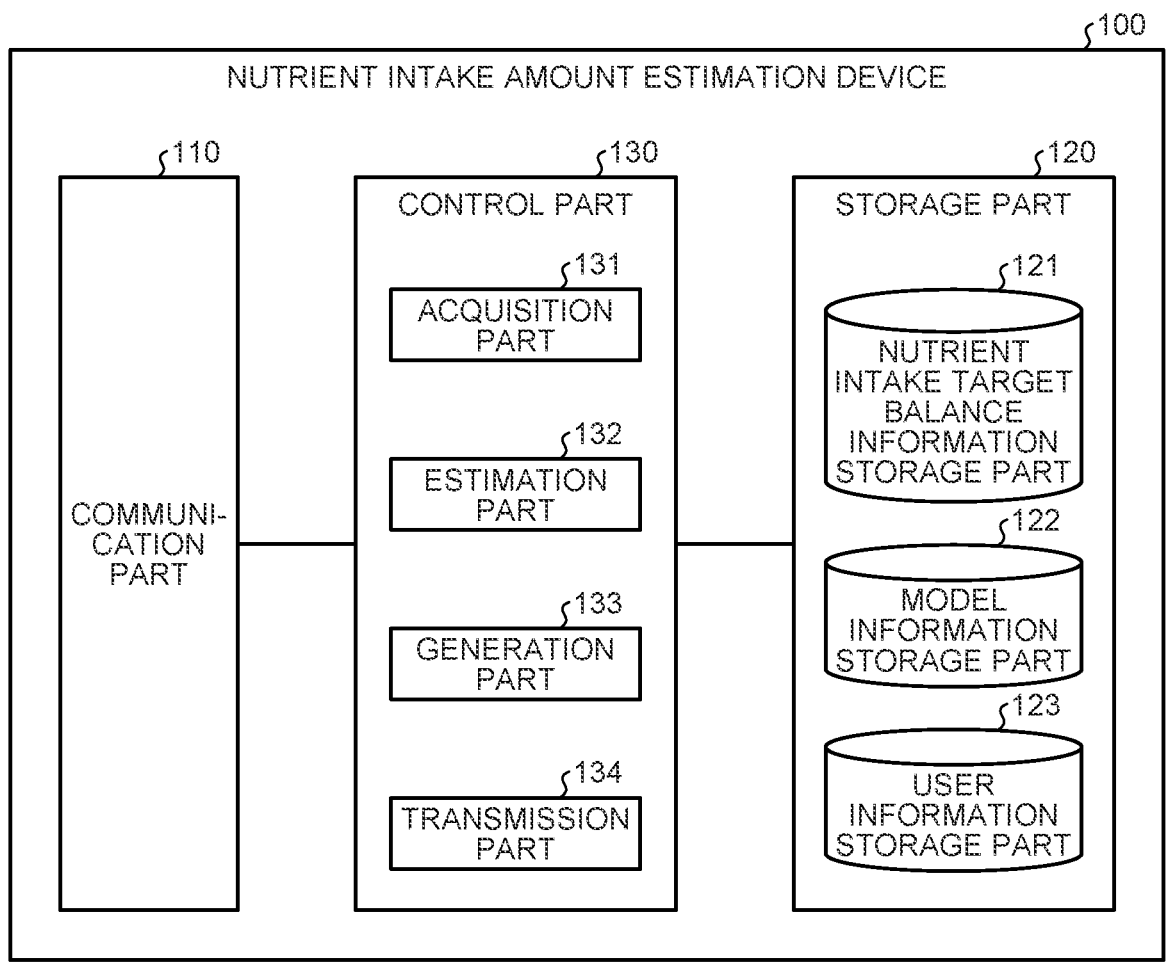
FIG. 4 is a block diagram illustrating an example of a configuration of a nutrient intake amount estimation device according to the embodiment.

First, the following describes a functional configuration of the nutrient intake amount estimation device with reference to FIG. 4. FIG. 4 is a block diagram illustrating an example of the configuration of the nutrient intake amount estimation device according to the embodiment.

As illustrated in FIG. 4, the nutrient intake amount estimation device 100 includes a communication part 110, a storage part 120, and a control part 130. The nutrient intake amount estimation device 100 may also include an input part (for example, a keyboard or a mouse) that receives various operations from an administrator and the like of the nutrient intake amount estimation device 100, or a display part (for example, a liquid crystal display) for displaying various kinds of information.

The communication part 110 is implemented by a communication circuit, for example. The communication part 110 is connected to the predetermined network N (refer to FIG. 3) in a wired or wireless manner, and transmits/receives information to/from an external information processing device. For example, the communication part 110 is connected to the predetermined network N (refer to FIG. 3) in a wired or wireless manner, and transmits/receives information to/from the user terminal 10, the toilet operation device, and the like.

For example, the storage part 120 is implemented by a semiconductor memory element such as a random access memory (RAM) and a flash memory, or a storage device such as a hard disk and an optical disc. For example, the storage part 120 is a computer-readable recording medium that non-transitorily records a nutrient intake balance estimation program, data used by the nutrient intake balance estimation program, and the like. As illustrated in FIG. 4, the storage part 120 according to the embodiment includes a nutrient intake target balance information storage part 121, a model information storage part 122, and a user information storage part 123.

The nutrient intake target balance information storage part according to the embodiment stores various kinds of information related to the nutrient intake target balance. For example, the nutrient intake target balance information storage part stores the nutrient intake balance that can be set by the user as a goal. FIG. 5 is a diagram illustrating an example of the nutrient intake target balance information storage part according to the embodiment. The nutrient intake target balance information storage part illustrated in FIG. 5 includes items such as "nutrient intake target balance ID", "name", and "nutrient ratio".

The "nutrient intake target balance ID" indicates identification information for identifying each nutrient intake target balance. The "name" indicates a name of the nutrient intake target balance.

The "nutrient ratio" indicates a nutrient ratio as a target of evaluation. The "nutrient ratio" in FIG. 5 includes items corresponding to three nutrients of "carbohydrates", "fat", and "protein". The "nutrient ratio" may include not only "carbohydrates", "fat", and "protein" but also items corresponding to nutrients to be monitored such as "vitamins", "minerals", "dietary fiber", "saccharides", and lactose or glucose as a component of saccharides.

In the example of FIG. 5, the nutrient intake balance (nutrient intake balance TB1) identified with the nutrient intake target balance ID of "TB1" is "Modern Standard". The nutrient intake balance TB1 indicates that the nutrient ratio including carbohydrates of "60%", fat of "25%", and protein of "15%" has an ideal balance.

The nutrient intake balance (nutrient intake balance TB2) identified with the nutrient intake target balance ID of "TB2" is "Athlete Diet". The nutrient intake balance TB2 indicates that the nutrient ratio including carbohydrates of "35%", fat of "25%", and protein of "40%" has an ideal balance.

The nutrient intake target balance information storage part 121 may store not only the information described above but also various kinds of information depending on a purpose. The six nutrient intake target balances in the nutrient intake target balance information storage part 121 illustrated in FIG. 5 are merely examples, and seven or more types of nutrient intake target balances may be included therein. Furthermore, a nutrient intake target balance including a determined nutrient ratio that is individually adjusted may be enabled to be set by the user by specifically designating (selecting) the nutrient ratio, or by determining the nutrient ratio appropriate for the user based on information about the user.

The model information storage part 122 according to the embodiment stores information related to the model. For example, the model information storage part 122 stores model information (model data) used for estimating a balance of nutrients that are estimated to be taken by the user. FIG. 6 is a diagram illustrating an example of the model information storage part according to the embodiment. For example, the model information storage part 122 stores information related to facilities. The model information storage part 122 illustrated in FIG. 6 includes items of "model ID", "type", and "model data".

The "model ID" indicates identification information for identifying a model. The "type" indicates a type of a corresponding model. The "model data" indicates data of a model. FIG. 6 illustrates an example in which conceptual information such as "MDT1" is stored in the "model data", but actually, the "model data" includes various kinds of information constituting the model such as a function or information related to the network included in the model.

In the example illustrated in FIG. 6, the type of the model (model M1) identified with the model ID of "M1" is "neural network". The model data of the model M1 is model data MDT1.

For example, the model M1 as a neural network is an estimation model of outputting, in accordance with an input based on the output value of the sensor device 50, information indicating a nutrient balance corresponding to the input. For example, the model M1 is a classifier (discriminator) that outputs, based on the output value of the sensor device 50 that has detected the excretion smell, information indicating the nutrient balance into which taken nutrients corresponding to the excretion smell are classified.

Alternatively, the model M1 may be a model of outputting a value (score) corresponding to each nutrient. For example, the model M1 may be a model of outputting, based on the output value of the sensor device 50 that has detected the excretion smell, scores indicating ratios of at least two nutrients among carbohydrates, fat, protein, vitamins, and minerals of the taken nutrients corresponding to the excretion smell.

The type of a model (model M2) identified with the model ID of "M2" is a "support vector machine". The model data of the model M2 is model data MDT2.

For example, the model M2 as a support vector machine (SVM) is an estimation model of outputting, in accordance with an input based on the output value of the sensor device 50, information indicating a nutrient balance corresponding to the input. For example, the model M2 is a classifier (discriminator) that outputs, based on the output value of the sensor device 50 that has detected the excretion smell, information indicating the nutrient balance into which the taken nutrients corresponding to the excretion smell are classified.

The type of a model (model M3) identified with the model ID of "M3" is a "random forest". The model data of the model M3 is model data MDT3.

For example, the model M3 as a random forest (decision tree) is an estimation model of outputting, in accordance with an input based on the output value of the sensor device 50, information indicating the nutrient balance corresponding to the input. For example, the model M3 is a classifier (discriminator) that outputs, based on the output value of the sensor device 50 that has detected the excretion smell, information indicating the nutrient balance into which the taken nutrients corresponding to the excretion smell are classified.

The type of a model (model M4) identified with the model ID of "M4" is a "logistic regression". The model data of the model M4 is model data MDT4.

For example, the model M4 as logistic regression is an estimation model of outputting, in accordance with an input based on the output value of the sensor device 50, information indicating the nutrient balance corresponding to the input. For example, the model M4 is a classifier (discriminator) that outputs, based on the output value of the sensor device 50 that has detected the excretion smell, information indicating the nutrient balance into which the taken nutrients corresponding to the excretion smell are classified.

The type of a model (model M5) identified with the model ID of "M5" is a "decision jungle". The type of a model (model M6) identified with the model ID of "M6" is "perceptron". The type of a model (model M7) identified with the model ID of "M7" is "Bayesian discrimination". The type of a model (model M8) identified with the model ID of "M8" is "k-nearest neighbor algorithm". The type of a model (model M9) identified with the model ID of "M9" is "hidden Markov model". The models M1 to M9 described above are merely examples, and the model information storage part 122 may store other types as models to be used as the estimation model, or may store ten or more models.

The model information storage part 122 may store not only the information described above but also various kinds of information depending on a purpose.

Figures 7, 8:
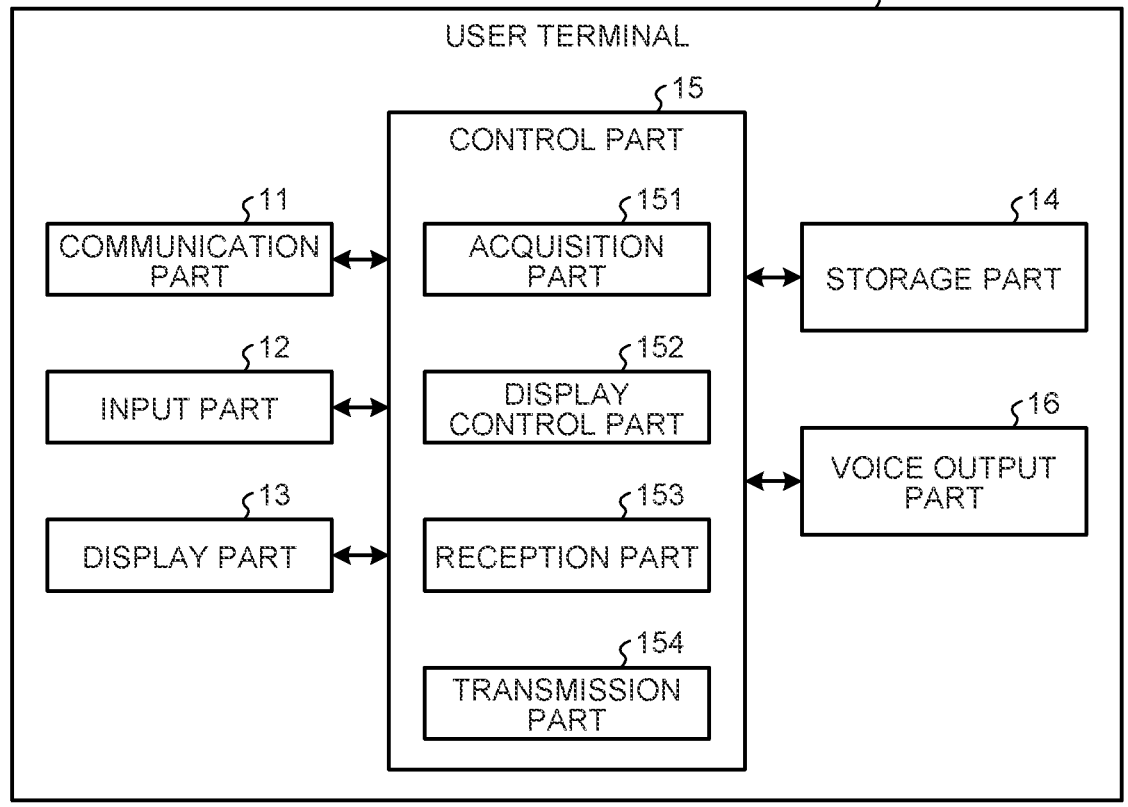
FIG. 7 is a diagram illustrating an example of a user information storage part according to the embodiment.
FIG. 8 is a block diagram illustrating an example of a configuration of a user terminal according to the embodiment.

The user information storage part 123 according to the embodiment stores various kinds of information related to the user. For example, the user information storage part 123 stores various kinds of information of the user who uses the nutrient intake amount estimation system 1. FIG. 7 is a diagram illustrating an example of the user information storage part according to the embodiment. The user information storage part 123 illustrated in FIG. 7 includes items such as "user ID", "attribute information", and "nutrient intake target balance".

The "user ID" indicates identification information for identifying the user. The "attribute information" stores various kinds of information related to an attribute of the user identified with the user ID. The attribute information is represented by an abstract reference sign such as "ATB1", but includes specific information such as an age and distinction of sex. The "attribute information" stores not only an age and distinction of sex but also various kinds of attribute information of the user such as other pieces of demographic attribute information and psychographic attribute information such as a lifestyle, curiosity, or interest. For example, the "attribute information" stores a body weight, a height, nationality and a place of residence, a religion, an activity amount, a state of excretion and the number of times thereof, stomach bloating, stomach oppression, a sleep state, presence/absence of a blind headache, a mental state, an incidence history of relatives, a dietary life (the number of times, timing, a way of eating, snacking, an eating speed, and drinking) and the like.

The "nutrient intake target balance" indicates a nutrient intake target balance corresponding to the user. For example, the "nutrient intake target balance" indicates a nutrient intake target balance that is set based on selection by the user, or information about the user.

For example, in the example of FIG. 7, the attribute information of the user (user U1) identified with the user ID of "U1" is "ATB1". The nutrient intake target balance of the user U1 is "TB1". That is, the nutrient intake target balance set to the user U1 is the nutrient balance of "Modern Standard" identified with the nutrient intake target balance ID of "TB1".

The user information storage part 123 may store not only the information described above but also various kinds of information depending on a purpose. The user information storage part 123 may store, in association with the user, behavior information indicating various kinds of behavior of the user such as a use history of an application such as the nutrient balance monitoring application by the user, positional information of the user, and the like.

Returning to FIG. 3, the description will be continued. For example, the control part 130 is implemented when a computer program stored in the nutrient intake amount estimation device 100 (for example, the nutrient intake balance estimation program according to the present disclosure) is executed by a central processing unit (CPU), a Graphics Processing Unit (GPU), and the like using a RAM and the like as a working area. The control part 130 is a controller, and implemented by an integrated circuit such as an application specific integrated circuit (ASIC) or a field programmable gate array (FPGA), for example.

As illustrated in FIG. 3, the control part 130 includes an acquisition part 131, an estimation part 132, a generation part 133, and a transmission part 134, and implements or executes a function or an operation of information processing described below. An internal configuration of the control part 130 is not limited to the configuration illustrated in FIG. 3, and may be another configuration that performs the information processing described later.

The acquisition part 131 functions as an acquisition unit. The acquisition part 131 acquires various kinds of information from the storage part 120. The acquisition part 131 receives various kinds of information from the nutrient intake amount output device such as the sensor device 50 and the user terminal 10. The acquisition part 131 receives the output value of the sensor device 50 from the sensor device 50. The acquisition part 131 receives, from the user terminal 10, information indicating the nutrient intake target balance selected by the user.

The estimation part 132 functions as an estimation unit. The estimation part 132 performs estimation processing by using a model stored in the model information storage part 122. The estimation part 132 estimates the estimated nutrient intake balance of the user by using an output of the estimation model that outputs information indicating a balance of nutrients that are estimated to be taken by the user in accordance with an input based on the output value of the sensor device 50.

The estimation part 132 performs estimation processing by using the output value of the sensor device 50 that has detected the excretion smell of the user, and the models M1 to M3 stored in the model information storage part 122. The estimation part 132 estimates the estimated nutrient intake balance of the user by using output results of the models M1 to M3 to which the output value of the sensor device 50 that has detected the excretion smell of the user is input. The estimation part 132 estimates which of the four balances including "well-balanced", "excessive in carbohydrates", "excessive in fat", and "excessive in protein" corresponds to the estimated nutrient intake balance of the user by using the output results of the models M1 to M3. Details about the estimation processing performed by the estimation part 132 will be described later with reference to FIG. 12.

The generation part 133 generates various kinds of information based on the information acquired by the acquisition part 131. The generation part 133 generates information by using the estimation result obtained by the estimation part 132. The generation part 133 generates an input value for the estimation model such as the model M1 by using the output value of the sensor device 50. For example, the generation part 133 generates the input value for the estimation model by extracting part of the output values of the sensor device 50 (for example, a peak value), or calculating a derivative of the output value of the sensor device 50.

The generation part 133 generates various kinds of information such as a screen (image information) to be provided to an external information processing device by appropriately using various techniques. The generation part 133 generates a screen (image information) and the like to be provided to the user terminal 10. For example, the generation part 133 generates a screen (image information) and the like to be provided to the user terminal 10 based on the information stored in the storage part 120.

Figure 14:
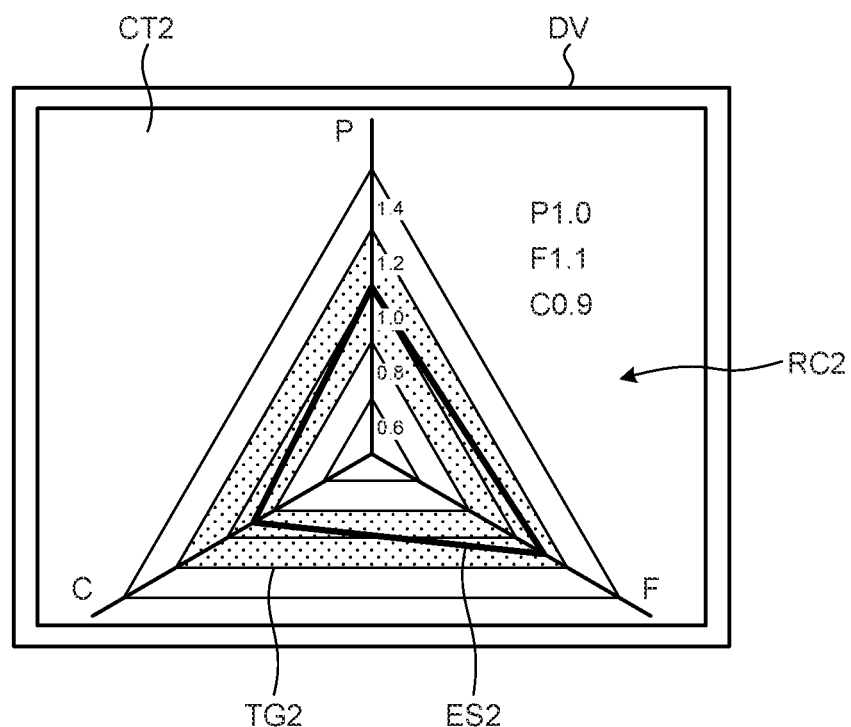
FIG. 14 is a diagram illustrating an example of display of a nutrient intake balance.
Figure 15:
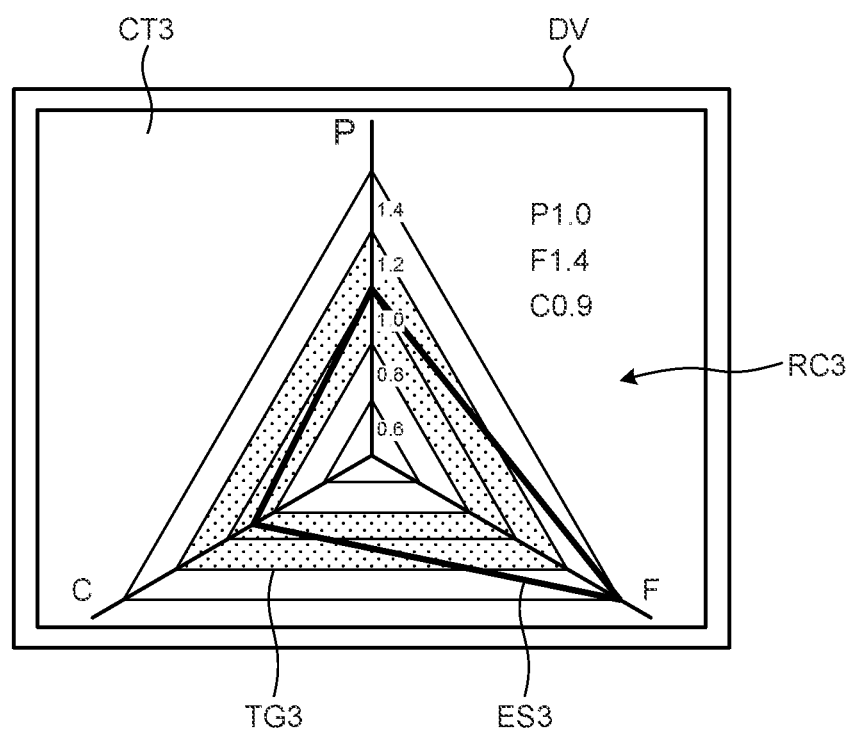
FIG. 15 is a diagram illustrating an example of display of the nutrient intake balance.
Figure 16:
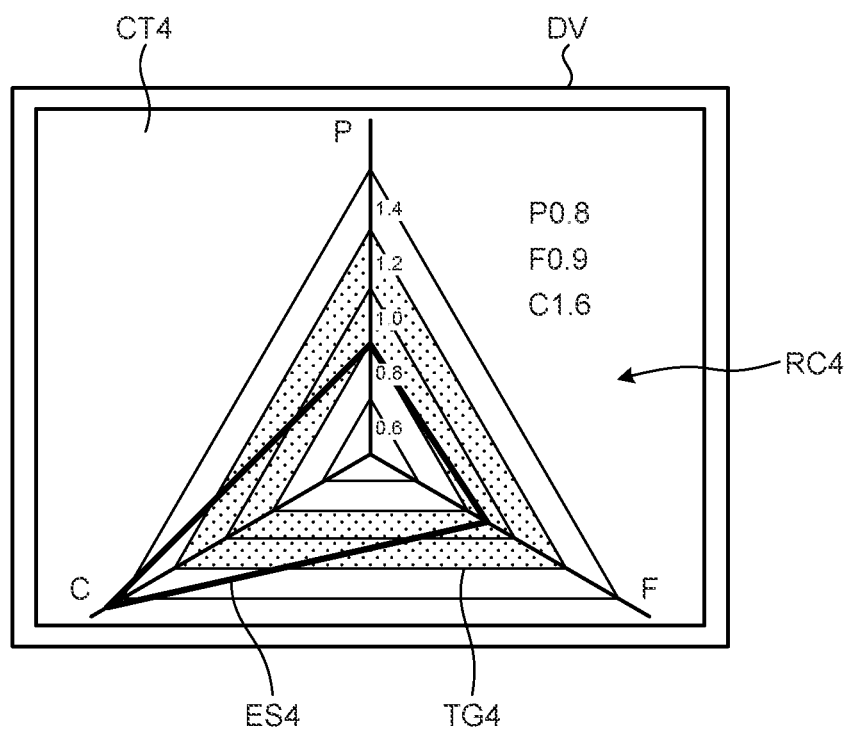
FIG. 16 is a diagram illustrating an example of display of the nutrient intake balance.

The generation part 133 generates content including the information indicating the nutrient intake target balance of the user and the information indicating the estimated nutrient intake balance of the user that is estimated by the estimation part 132. The generation part 133 generates content obtained by superimposing the estimated nutrient intake balance of the user estimated by the estimation part 132 on the nutrient intake target balance of the user. In the example of FIG. 1, the generation part 133 generates the content CT1. The generation part 133 also generates pieces of content CT2 to CT4 as illustrated in FIG. 14 to FIG. 16.

The generation part 133 may generate a screen (image information) and the like by any processing so long as a screen (image information) and the like to be provided to an external information processing device can be generated. For example, the generation part 133 generates a screen (image information) to be provided to the user terminal 10 by appropriately using various techniques related to image generation, image processing, and the like. For example, the generation part 133 generates the screen (image information) to be provided to the user terminal 10 by appropriately using various techniques such as Java (registered trademark). The generation part 133 may generate the screen (image information) to be provided to the user terminal 10 based on a format of Cascading Style Sheets (CSS), JavaScript (registered trademark), or Hyper Text Markup Language (HTML). For example, the generation part 133 may generate the screen (image information) in various formats such as Joint Photographic Experts Group (JPEG), Graphics Interchange Format (GIF), and Portable Network Graphics (PNG).

The transmission part 134 functions as a transmission unit. The transmission part 134 transmits information to an external information processing device. For example, the transmission part 134 transmits various kinds of information to the sensor device 50 or the nutrient intake amount output device such as the user terminal 10. The transmission part 134 transmits the information estimated by the estimation part 132 to the user terminal 10. The transmission part 134 transmits the information generated by the generation part 133 to the user terminal 10. In the example of FIG. 1, the transmission part 134 transmits the content CT1 to the user terminal 10.

4-2. Functional Configuration of User Terminal

Next, the following describes a functional configuration of the user terminal 10 as an example of the nutrient intake amount output device with reference to FIG. 8. FIG. 8 is a block diagram illustrating an example of the configuration of the user terminal according to the embodiment.

As illustrated in FIG. 8, the user terminal 10 includes a communication part 11, an input part 12, a display part 13, a storage part 14, a control part 15, and a voice output part 16.

For example, the communication part 11 is implemented by an NIC, a communication circuit, and the like. The communication part 11 is connected to the network N (the Internet and the like) in a wired or wireless manner, and transmits/receives information to/from another device and the like such as the nutrient intake amount estimation device 100 via the network N.

The input part 12 receives inputs of various operations from the user. The input part 12 receives inputs of various kinds of information via the display part 13. The input part 12 has a function of detecting a voice. For example, the input part 12 includes a keyboard or a mouse connected to the user terminal 10. The input part 12 may also include a button disposed on the user terminal 10, or a microphone that detects a voice.

For example, the input part 12 may include a touch panel capable of implementing a function equivalent to that of a keyboard or a mouse. In this case, the input part 12 receives various operations from the user via a display screen by a function of the touch panel implemented by various sensors. That is, the input part 12 receives various operations from the user via the display part 13 of the user terminal 10. For example, the input part 12 receives an operation such as a designating operation performed by the user via the display part 13 of the user terminal 10. For example, the input part 12 functions as a reception part that receives a user's operation by the function of the touch panel. In this case, the input part 12 may be integrated with a reception part 153. As a scheme for detecting a user's operation by the input part 12, an electrostatic capacitance scheme is mainly employed for a tablet terminal, but any scheme capable of detecting a user's operation and implementing the function of the touch panel may be employed such as a resistance film scheme, a surface acoustic wave scheme, an infrared scheme, or an electromagnetic induction scheme as another detection scheme.

The display part 13 functions as an output part (output unit) that outputs various kinds of information. The display part 13 is disposed on the user terminal 10 to display various kinds of information. For example, the display part 13 is implemented by a liquid crystal display, an organic Electro-Luminescence (EL) display, and the like. The display part 13 may be implemented by any unit capable of displaying the information provided from the nutrient intake amount estimation device 100. The display part 13 displays various kinds of information in accordance with control by a display control part 152.

In the example of FIG. 1, the display part 13 displays the content CT1. The display part 13 also displays the pieces of content CT2 to CT4 as illustrated in FIG. 14 to FIG. 16. For example, the user terminal 10 executes a computer program (output program) for outputting the nutrient intake amount, and displays the estimated nutrient intake balance on the display part 13. An output mode of the user terminal 10 is not limited to display, and may be another output mode such as an output by voice. The user terminal 10 may output the estimated nutrient intake balance by voice using the voice output part 16.

The storage part 14 is, for example, implemented by a semiconductor memory element such as a RAM or a flash memory, or a storage device such as a hard disk or an optical disc. The storage part 14 stores various kinds of information used for displaying information. The storage part 14 stores various kinds of information such as an output program for outputting the estimated nutrient intake balance. For example, the storage part 14 stores an output program for displaying the nutrient intake target balance and the nutrient intake balance. For example, the output program may be an application installed in the user terminal 10 (the nutrient balance monitoring application and the like) for displaying the nutrient balance.

Returning to FIG. 8, the description will be continued. For example, the control part 15 is implemented when a computer program stored in the user terminal 10 (for example, a display program such as an information processing program according to the present disclosure) is executed by a CPU, an MPU, or the like using a RAM and the like as a working area. The control part 15 is a controller, and may be implemented by an integrated circuit such as an ASIC or an FPGA, for example.

As illustrated in FIG. 8, the control part 15 includes an acquisition part 151, the display control part 152, the reception part 153, and a transmission part 154, and implements or executes a function or an operation of information processing described below. An internal configuration of the control part 15 is not limited to the configuration illustrated in FIG. 8, and may be another configuration that performs the information processing described later.

The acquisition part 151 acquires various kinds of information. The acquisition part 151 acquires various kinds of information from the storage part 14. The acquisition part 151 receives various kinds of information from another information processing device such as the nutrient intake amount estimation device 100.

The acquisition part 151 receives information indicating the nutrient intake target balance or the nutrient intake balance from the nutrient intake amount estimation device 100. The acquisition part 151 receives content from the nutrient intake amount estimation device 100. In the example of FIG. 1, the acquisition part 151 receives the content CT1.

The display control part 152 functions as an output control part that controls output of various kinds of information. The display control part 152 controls display of the display part 13. The display control part 152 controls display of the display part 13 based on the information received by the acquisition part 151. The display control part 152 controls display of the display part 13 based on the information received by the reception part 153. The display control part 152 controls display of the display part 13 so that the content CT1 is displayed by the display part 13.

The reception part 153 receives various kinds of information. For example, the reception part 153 receives an input from the user via the input part 12. The reception part 153 receives an operation performed by the user. The reception part 153 receives a user's operation on the information displayed by the display part 13. The reception part 153 receives an utterance of the user as an input. The reception part 153 receives designation of the nutrient intake target balance by the user.

In the example of FIG. 1, the reception part 153 receives an input by the user U1. The reception part 153 receives designation of the nutrient intake target balance by the user U1.

The transmission part 154 transmits various kinds of information to an external information processing device. For example, the transmission part 154 transmits various kinds of information to another information processing device such as the user terminal 10. The transmission part 154 transmits information stored in the storage part 14.

In the example of FIG. 1, the transmission part 154 transmits the goal of the user U1 received by the reception part 153 to the nutrient intake amount estimation device 100.

The voice output part 16 outputs various kinds of information. The voice output part 16 has a function of outputting a voice. For example, the voice output part 16 includes a speaker that outputs a voice. The voice output part 16 outputs information by voice to the user. The voice output part 16 outputs information displayed by the display part 13 by voice. For example, the voice output part 16 outputs information included in the content CT1 by voice.

The user terminal 10 may implement processing such as display by the display part 13 and reception of an operation as described above by a predetermined application (the nutrient balance monitoring application and the like). The user terminal 10 may acquire a script executed on a predetermined software application, and perform information processing such as information display or operation reception as described above by using control information such as the acquired script. For example, the control information corresponds to a computer program that implements information processing such as information display or operation reception by the user terminal 10 according to the embodiment, and is implemented by CSS, JavaScript (registered trademark), HTML, or an optional language with which the information processing such as information display or operation reception by the user terminal 10 described above can be written. For example, processing such as display control processing and reception processing performed by the control part 15 may be implemented by the nutrient balance monitoring application. In a case in which the display control processing, the reception processing, or the like described above is performed by a dedicated application, for example, the control part 15 may include an application control part that controls a predetermined application (for example, a Web browser) or the dedicated application.

The user terminal 10 may receive the nutrient intake target balance and the nutrient intake balance from the nutrient intake amount estimation device 100, generate content by using the received nutrient intake target balance and nutrient intake balance, and display the generated content. In this case, the user terminal 10 may include a generation part having a function similar to that of the generation part 133 (refer to FIG. 4).

5. Processing Procedure

Figure 9:
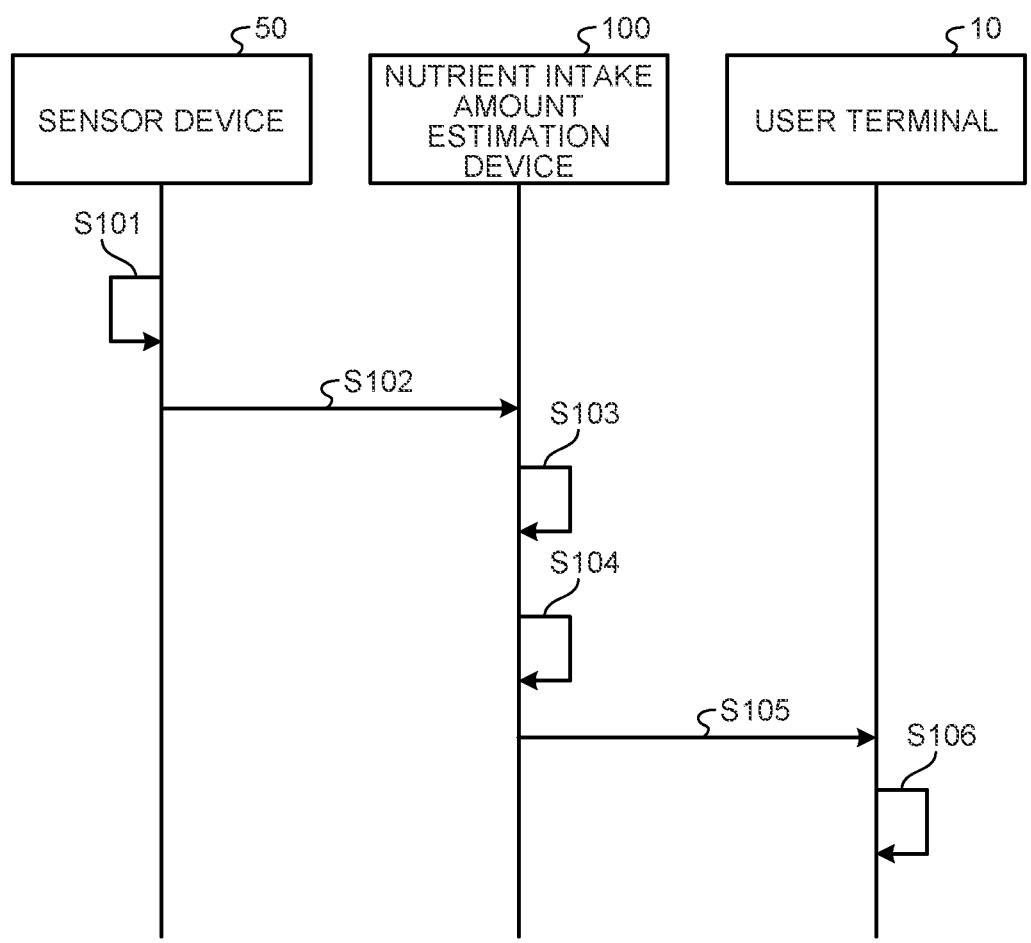
FIG. 9 is a sequence diagram illustrating an example of nutrient intake amount estimation processing according to the embodiment.
Figure 10:
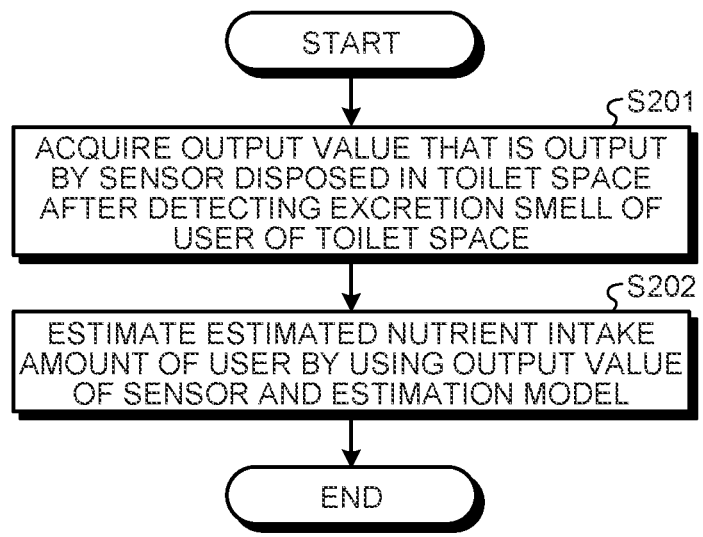
FIG. 10 is a flowchart illustrating an example of a processing procedure performed by the nutrient intake amount estimation device.
Figure 11:
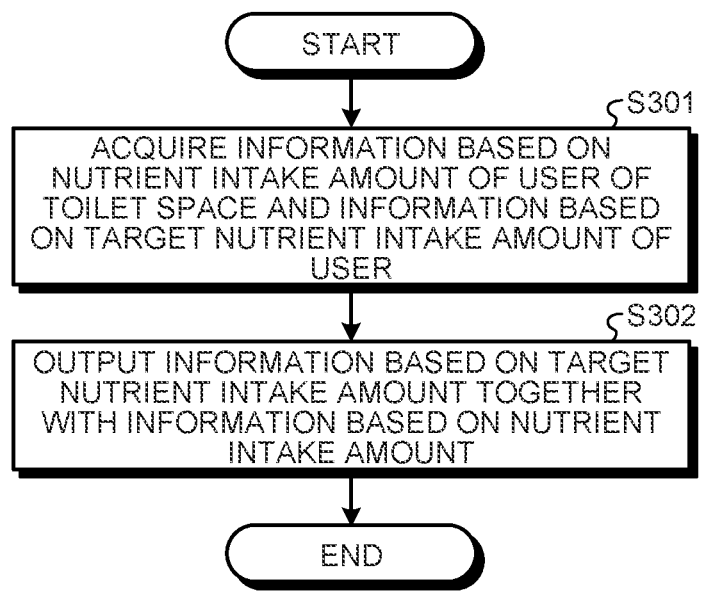
FIG. 11 is a flowchart illustrating an example of a processing procedure performed by the nutrient intake amount output device.

The following describes a processing procedure related to the embodiment with reference to FIG. 9 to FIG. 11.

5-1. Processing of Nutrient Intake Amount Estimation System

Next, the following describes a processing sequence of the nutrient intake amount estimation system 1 with reference to FIG. 9. FIG. 9 is a sequence diagram illustrating an example of nutrient intake amount estimation processing according to the embodiment. For example, in a case in which excretion is detected (also referred to as a "second trigger") after the user is detected (also referred to as a "first trigger"), the nutrient intake amount estimation system 1 starts to detect an excretion smell. For example, the first trigger is detection of the user seated on the toilet seat. For example, the second trigger is detection of a specific gas such as hydrogen sulfide or hydrogen. The first trigger and the second trigger are not limited to those described above. For example, the first trigger may be detection of the user entering the toilet space. For example, the second trigger may be detection of presence/absence of excrement by an image sensor, an infrared sensor, a voice sensor, a temperature sensor, or the like. Alternatively, for example, the second trigger may be detection of a posture change of the user by a strain sensor disposed on the toilet seat. For example, the second trigger may be an elapsed time from the first trigger. The triggers described above are merely examples, and various triggers may be employed as a trigger for detection processing of gas (excretion smell).

First, the sensor device 50 detects an excretion smell of the user of the toilet space (Step S101). The sensor device 50 transmits an output value based on the detected excretion smell to the nutrient intake amount estimation device 100 (Step S102).

The nutrient intake amount estimation device 100 that has received the output value from the sensor device 50 performs estimation processing (Step S103). The nutrient intake amount estimation device 100 inputs, to the estimation model, an input value generated by using the output value of the sensor device 50, and estimates the estimated nutrient intake balance of the user based on an output of the estimation model. The nutrient intake amount estimation device 100 generates content to be provided to the user based on an estimation result (Step S104).

The nutrient intake amount estimation device 100 transmits the generated content to the user terminal 10 used by the user (Step S105). The user terminal 10 that has received the content displays the content (Step S106).

5-2. Processing of Nutrient Intake Amount Estimation Device

First, the following describes a processing flow of the nutrient intake amount estimation processing with reference to FIG. 10. FIG. 10 is a flowchart illustrating an example of a processing procedure performed by the nutrient intake amount estimation device.

The nutrient intake amount estimation device 100 acquires an output value that is output by a sensor disposed in the toilet space after detecting the excretion smell of the user of the toilet space (Step S201).

The nutrient intake amount estimation device 100 estimates the estimated nutrient intake amount of the user by using the output value of the sensor and the estimation model (Step S202). For example, the nutrient intake amount estimation device 100 inputs an input value based on the output value of the sensor to the estimation model, and estimates the estimated nutrient intake balance of the user by using information output by the estimation model.

5-3. Processing of Nutrient Intake Amount Output Device

Next, the following describes a processing flow of output processing of the nutrient intake balance with reference to FIG. 11. FIG. 11 is a flowchart illustrating an example of a processing procedure performed by the nutrient intake amount output device. FIG. 11 exemplifies a case in which the user terminal 10 as an example of the nutrient intake amount output device performs the output processing of the nutrient intake balance. An execution subject of the output processing of the nutrient intake balance is not limited to the user terminal 10, and may be another nutrient intake amount output device such as the toilet operation device, for example.

The user terminal 10 acquires information based on the nutrient intake of the user of the toilet space and information based on the target nutrient intake of the user (Step S301). For example, the user terminal 10 receives, from the nutrient intake amount estimation device 100, content including the estimated nutrient intake balance of the user estimated by the nutrient intake amount estimation device 100 and the nutrient intake target balance of the user.

The user terminal 10 outputs information based on the target nutrient intake together with the information based on the nutrient intake (Step S302). For example, the user terminal 10 displays content obtained by superimposing the nutrient intake target balance of the user on the estimated nutrient intake balance of the user.

The user terminal 10 may generate content obtained by superimposing the nutrient intake target balance of the user on the estimated nutrient intake balance of the user. In this case, in a case of acquiring the information about the nutrient intake balance of the user and the information about the nutrient intake target balance of the user, the user terminal 10 generates content obtained by superimposing the nutrient intake target balance of the user on the estimated nutrient intake balance of the user. The user terminal 10 then displays the generated content. For example, the user terminal 10 generates the content CT1 in FIG. 1, and displays the generated content CT1.

6. Nutrient Intake Balance Estimation

Figure 12:
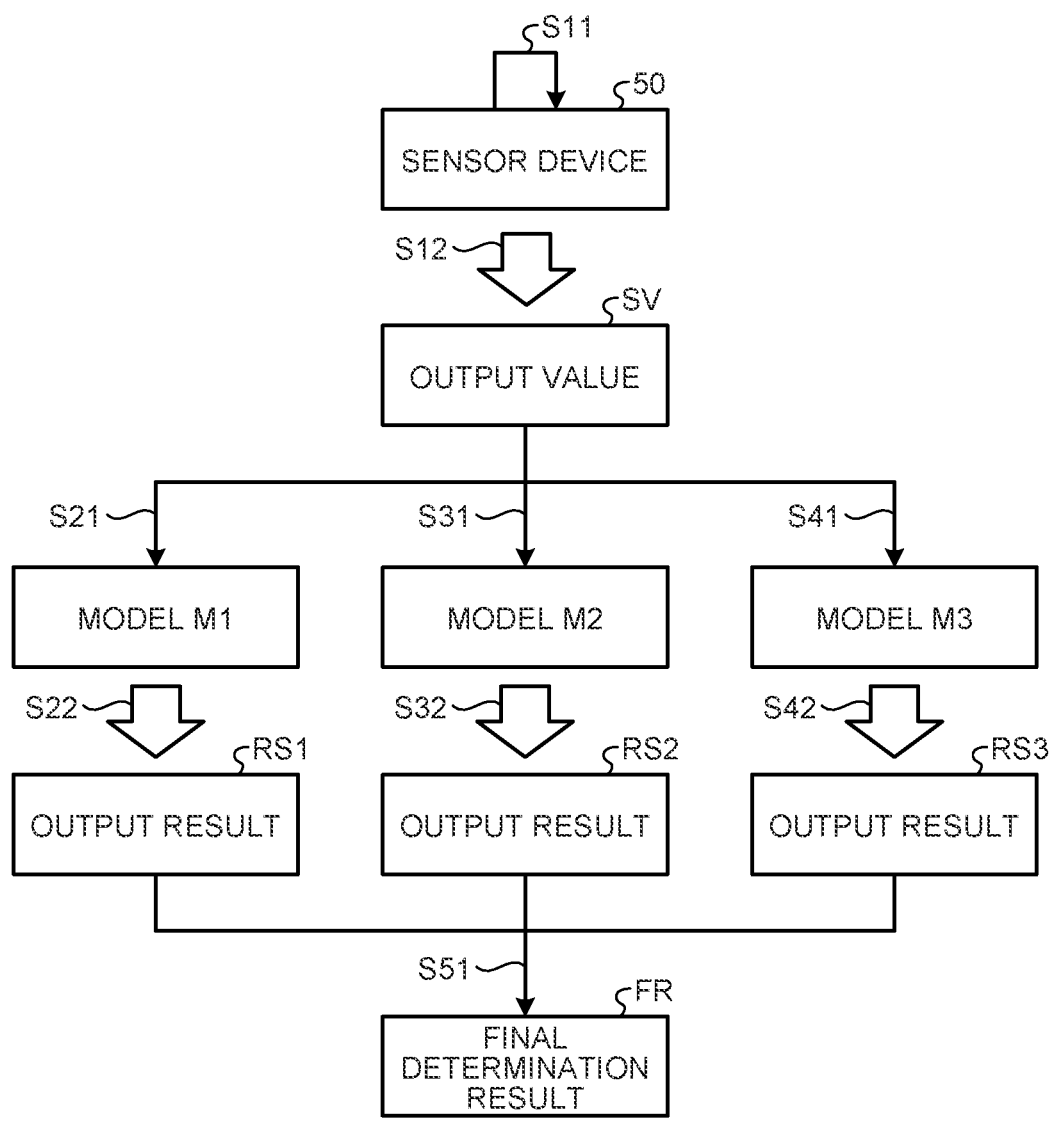
FIG. 12 is a diagram illustrating an example of nutrient intake balance estimation.

The following conceptually describes processing of nutrient intake balance estimation with reference to FIG. 12. FIG. 12 is a diagram illustrating an example of nutrient intake balance estimation. The following describes each piece of processing in FIG. 12 by exemplifying the case of FIG. 1. As described above, the three models including the models M1 to M3 are exemplified, but the models to be used may be the other models such as M4 to M9, or four or more models may be used.

First, the sensor device 50 disposed in the toilet space PS1 detects the excretion smell of the user U1 (Step S11). The sensor device 50 then outputs an output value SV corresponding to the detection of the excretion smell of the user U1 (Step S12).

The nutrient intake amount estimation device 100 inputs an input value generated by using the output value SV to each of the models M1 to M3, and acquires estimation results of the respective models M1 to M3. The nutrient intake amount estimation device 100 inputs the input value generated by using the output value SV to the model M1 (Step S21). The model M1 outputs an output result RS1 indicating which of the four balances including "well-balanced", "excessive in carbohydrates", "excessive in fat", and "excessive in protein" corresponds to the estimated nutrient intake balance of the user U1 in accordance with the input based on the output value SV (Step S22).

The nutrient intake amount estimation device 100 inputs the input value generated by using the output value SV to the model M2 (Step S31). The model M2 outputs an output result RS2 indicating which of the four balances including "well-balanced", "excessive in carbohydrates", "excessive in fat", and "excessive in protein" corresponds to the estimated nutrient intake balance of the user U1 in accordance with the input based on the output value SV (Step S32).

The nutrient intake amount estimation device 100 inputs the input value generated by using the output value SV to the model M3 (Step S41). The model M3 outputs an output result RS3 indicating which of the four balances including "well-balanced", "excessive in carbohydrates", "excessive in fat", and "excessive in protein" corresponds to the estimated nutrient intake balance of the user U1 in accordance with the input based on the output value SV (Step S42).

The nutrient intake amount estimation device 100 estimates a final determination result by using the three output results as the output results RS1 to RS3 of the respective three models M1 to M3 (Step S51). The nutrient intake amount estimation device 100 estimates which of the four balances including "well-balanced", "excessive in carbohydrates", "excessive in fat", and "excessive in protein" corresponds to the estimated nutrient intake balance of the user U1 by a majority vote of the output results RS1 to RS3. For example, in a case in which classifications of two or more of the output results RS1 to RS3 are the same, the nutrient intake amount estimation device 100 estimates that the classification corresponds to the estimated nutrient intake balance of the user U1. For example, in a case in which two or more output results are "excessive in fat", the nutrient intake amount estimation device 100 estimates that the estimated nutrient intake balance of the user U1 is "excessive in fat" based on the classification.

In this way, the nutrient intake amount estimation device 100 estimates the final determination result indicating inclination of meals taken by the user by a majority vote of derivation results of three types of independent algorithms. Due to this, the nutrient intake amount estimation system 1 can estimate inclination of meals taken by an individual such as the nutrient intake balance from the excretion smell via the output value of the sensor device 50 and the algorithm without investigating a specific gas type or concentration.

In a case in which classifications of all of the output results RS1 to RS3 are different from each other, the nutrient intake amount estimation device 100 may estimate the estimated nutrient intake balance of the user U1 based on a predetermined standard. In a case in which the classifications of all of the output results RS1 to RS3 are different from each other, the nutrient intake amount estimation device 100 may estimate the classification indicated by the output result of the model having the highest reliability to be the estimated nutrient intake balance of the user U1. For example, in a case in which the classifications of all of the output results RS1 to RS3 are different from each other, the nutrient intake amount estimation device 100 may estimate the classification indicated by the output result of the model M1 having the highest reliability to be the estimated nutrient intake balance of the user U1. For example, the nutrient intake amount estimation device 100 may calculate an accuracy rate of each model by using a history of classifications estimated by the respective models in the past and information indicating accuracy or inaccuracy thereof, and may cause the calculated accuracy rate of each model to be reliability of each model.

7. Sensor Output

Figure 13:
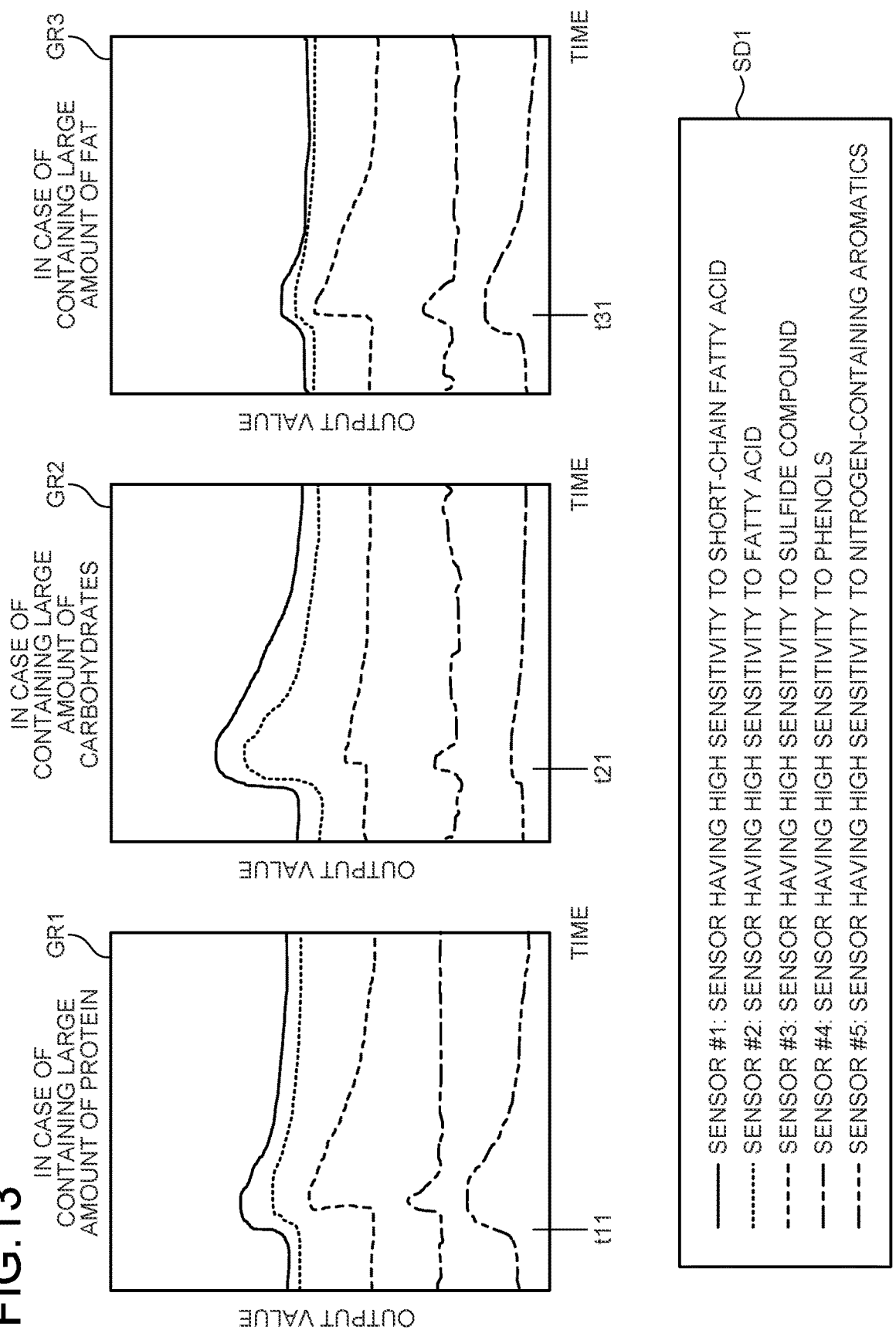
FIG. 13 is a diagram illustrating an example of an output value of a sensor.

The following describes an output of the sensor with reference to FIG. 13. FIG. 13 is a diagram illustrating an example of the output value of the sensor. In the example of FIG. 13, the sensor device 50 includes five sensors including a sensor #1, a sensor #2, a sensor #3, a sensor #4, and a sensor #5 (hereinafter, referred to as "sensors #1 to #5" in some cases).

In the example of FIG. 13, the sensor #1 is a sensor having high sensitivity to a short-chain fatty acid. The sensor #2 is a sensor having high sensitivity to a fatty acid. The sensor #3 is a sensor having high sensitivity to a sulfide compound. The sensor #4 is a sensor having high sensitivity to phenols. The sensor #5 is a sensor having high sensitivity to nitrogen-containing aromatics. The sensors #1 to #5 described above are merely examples, and all sensors having different sensitivities may be used.

Graphs GR1 to GR3 in FIG. 13 represent detection results in a case in which the sensors #1 to #5 detect the excretion smell. In a case in which the sensors #1 to #5 are semiconductor sensors, the output value is an output voltage. In the graphs GR1 to GR3, the output value of the sensor #1 is represented by a solid line, the output value of the sensor #2 is represented by a dotted line, the output value of the sensor #3 is represented by a dashed line, the output value of the sensor #4 is represented by an alternate long and short dash line, and the output value of the sensor #5 is represented by a two-dot chain line.

The graph GR1 represents a detection result of the excretion smell in a case of a meal type containing a large amount of protein. A time t11 in the graph GR1 indicates a timing at which the smell is generated. The graph GR2 represents a detection result of the excretion smell in a case of a meal type containing a large amount of carbohydrates. A time t21 in the graph GR2 indicates a timing at which the smell is generated. The graph GR3 represents a detection result of the excretion smell in a case of a meal type containing a large amount of fat. A time t31 in the graph GR3 indicates a timing at which the smell is generated.

For example, the nutrient intake amount estimation device 100 acquires output values of the respective sensors #1 to #5 as represented by the graph GR1 from the sensor device 50, and generates input values to be input to the estimation models such as the models M1 to M3 based on the acquired output values of the sensors #1 to #5. In this case, each of the input values generated by the nutrient intake amount estimation device 100 based on the output values of the sensors #1 to #5 may be any value that indicates a characteristic of reaction of each of the sensors #1 to #5. For example, the input value generated by the nutrient intake amount estimation device 100 may indicate a characteristic such as a degree or change of reaction of each of the sensors #1 to #5.

As represented by the graphs GR1 to GR3, reactions of the sensors #1 to #5 are different depending on the meal type, that is, the balance of nutrients taken by a monitoring object person (user of the toilet space). The nutrient intake amount estimation system 1 converts a difference in output values at the time when a plurality of sensors such as the sensors #1 to #5 sense the excretion smell, return of a value after time has elapsed, and the like into numerical values. For example, the nutrient intake amount estimation device 100 generates the input value to be input to the estimation model by conversion into a numerical value. In this case, the nutrient intake amount estimation device 100 generates the input value that has been converted into a numerical value based on the output values of the respective sensors #1 to #5. In this case, the input value that is generated by the nutrient intake amount estimation device 100 based on the output values of the respective sensors #1 to #5 may be any value that indicates a characteristic of a reaction of each of the sensors #1 to #5. For example, the input value generated by the nutrient intake amount estimation device 100 may be a value indicating a characteristic such as a degree or change of the reaction of each of the sensors #1 to #5.

For example, the nutrient intake amount estimation device 100 acquires, from the sensor device 50, the output value of each of the sensors #1 to #5 as represented by the graph GR2, and generates the input value indicating the characteristic of the reaction of each of the sensors #1 to #5 based on the acquired output value of each of the sensors #1 to #5. The nutrient intake amount estimation device 100 then inputs the generated input value to the estimation model such as the models M1 to M3, and estimates the nutrient balance based on the output result of the estimation model.

As represented by the graphs GR1 to GR3, the sensors #1 to #5 have different waveforms, and inclination of numerical values are different among the sensors #1 to #5 depending on each meal group (nutrient intake balance). In this way, by using several types of sensors having different sensitivities such as the sensors #1 to #5, the nutrient intake amount estimation system 1 can improve identification (resolution) of the meal group (nutrient intake balance).

The sensor device 50 may include any type of sensor such as a chemoregister, a chemocapacitor, a chemodiode, a chemotransistor, a thermo-chemosensor, a mass sensitivity chemosensor, a fiber-type chemosensor, an electrochemical-type chemosensor, or a resonance-type chemosensor. In this way, a detection target the smell of which is detected by the sensor device 50 may be various such as capacitance, a voltage-current characteristic, a temperature, a refractive index, fluorescence intensity and a spectrum, impedance, or a resonance frequency.

8. Display Example Based on Estimation Result

The following describes a display example based on the estimation result with reference to FIG. 14 to FIG. 21.

First, the following describes a display example of the estimation result in a case of "well-balanced" with reference to FIG. 14. FIG. 14 is a diagram illustrating an example of display of the nutrient intake balance. A nutrient intake amount output device DV illustrated in FIG. 14 may be the user terminal 10, or may be another device.

The nutrient intake amount estimation device 100 generates the content CT2 including a radar chart RC2 obtained by superimposing an estimation chart ES2 corresponding to the estimated nutrient intake balance of the user on a target chart TG2 corresponding to the nutrient intake target balance of the user. The nutrient intake amount estimation device 100 transmits the content CT2 to the nutrient intake amount output device DV.

The nutrient intake amount output device DV that has received the content CT2 displays the content CT2. The estimation chart ES2 indicates that the estimation value of carbohydrates is 0.9, the estimation value of fat is 1.1, and the estimation value of protein is 1.0. The estimation chart ES2 indicates that all items fall within the target chart TG2, and the estimated nutrient intake balance is "well-balanced".

Next, the following describes a display example of the estimation result in a case of "excessive in fat" with reference to FIG. 15. FIG. 15 is a diagram illustrating an example of display of the nutrient intake balance. The nutrient intake amount output device DV illustrated in FIG. 15 may be the user terminal 10, or may be another device.

The nutrient intake amount estimation device 100 generates the content CT3 including a radar chart RC3 obtained by superimposing an estimation chart ES3 corresponding to the estimated nutrient intake balance of the user on a target chart TG3 corresponding to the nutrient intake target balance of the user. The nutrient intake amount estimation device 100 transmits the content CT3 to the nutrient intake amount output device DV.

The nutrient intake amount output device DV that has received the content CT3 displays the content CT3. The estimation chart ES3 indicates that the estimation value of carbohydrates is 0.9, the estimation value of fat is 1.4, and the estimation value of protein is 1.0. The estimation chart ES3 indicates that a significantly larger amount of fat than a target ratio is taken.

Next, the following describes a display example of the estimation result in a case of "excessive in carbohydrates" with reference to FIG. 16. FIG. 16 is a diagram illustrating an example of display of the nutrient intake balance. The nutrient intake amount output device DV illustrated in FIG. 16 may be the user terminal 10, or may be another device.

The nutrient intake amount estimation device 100 generates the content CT4 including a radar chart RC4 obtained by superimposing an estimation chart ES4 corresponding to the estimated nutrient intake balance of the user on a target chart TG4 corresponding to the nutrient intake target balance of the user. The nutrient intake amount estimation device 100 transmits the content CT4 to the nutrient intake amount output device DV.

The nutrient intake amount output device DV that has received the content CT4 displays the content CT3. The estimation chart ES4 indicates that the estimation value of carbohydrates is 1.6, the estimation value of fat is 0.9, and the estimation value of protein is 0.8. The estimation chart ES4 indicates that a significantly larger amount of carbohydrates than a target ratio is taken.

The information to be displayed based on the estimation result is not limited to the radar chart, and may be a graph in another format such as a bar graph, a line graph, a pie graph, or a bubble chart in which an amount is represented by a size of a circle, or character information. A display mode of displaying a plurality of these pieces of information may also be employed. This point will be described below with reference to FIG. 17 to FIG. 20.

Figure 17:
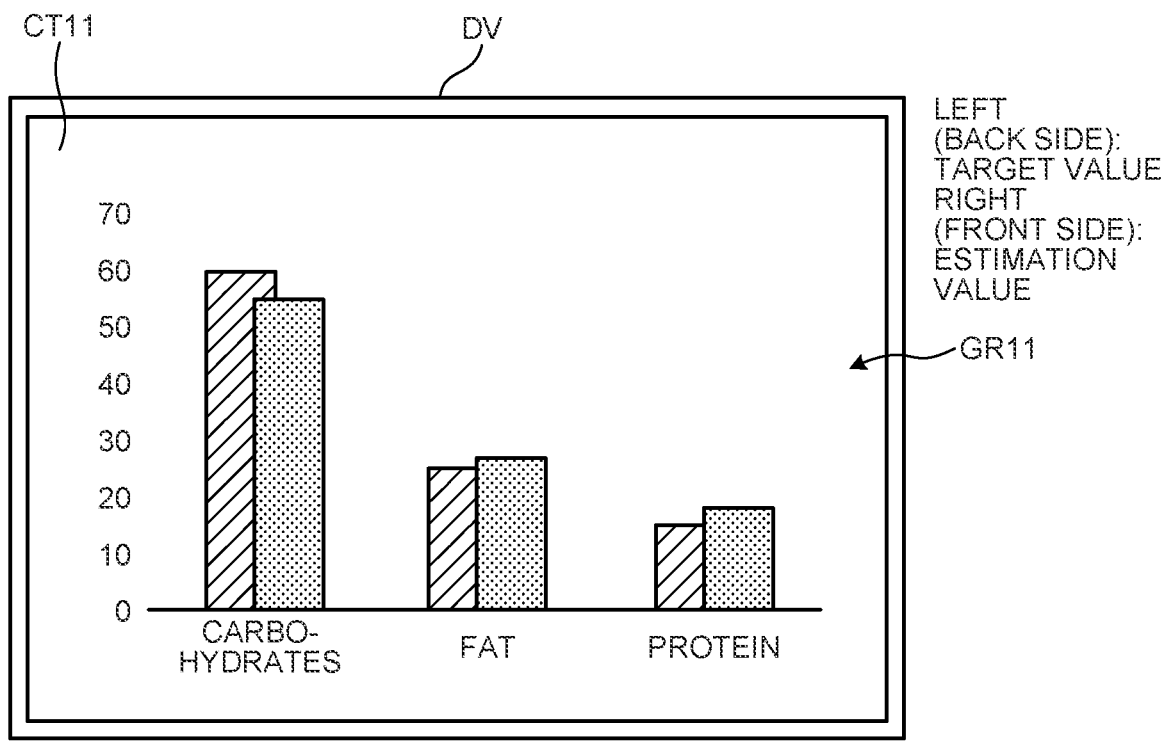
FIG. 17 is a diagram illustrating a modification of display of the nutrient intake balance.
Figure 18:
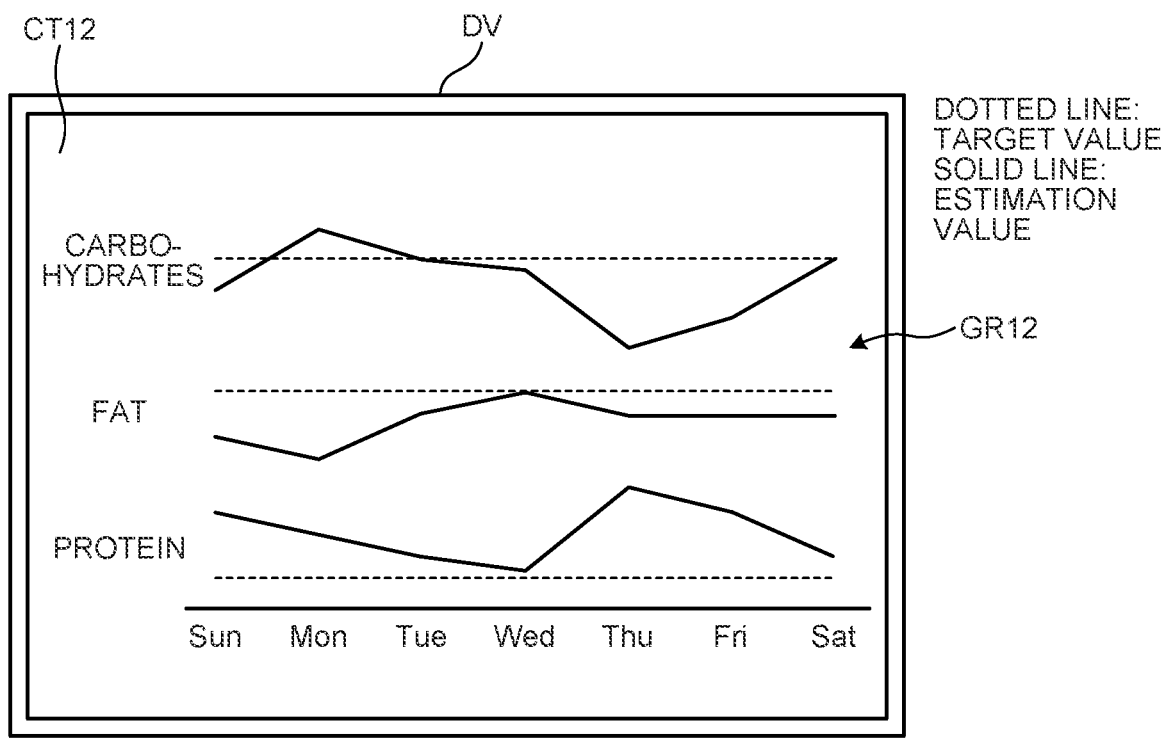
FIG. 18 is a diagram illustrating a modification of display of the nutrient intake balance.
Figure 19:
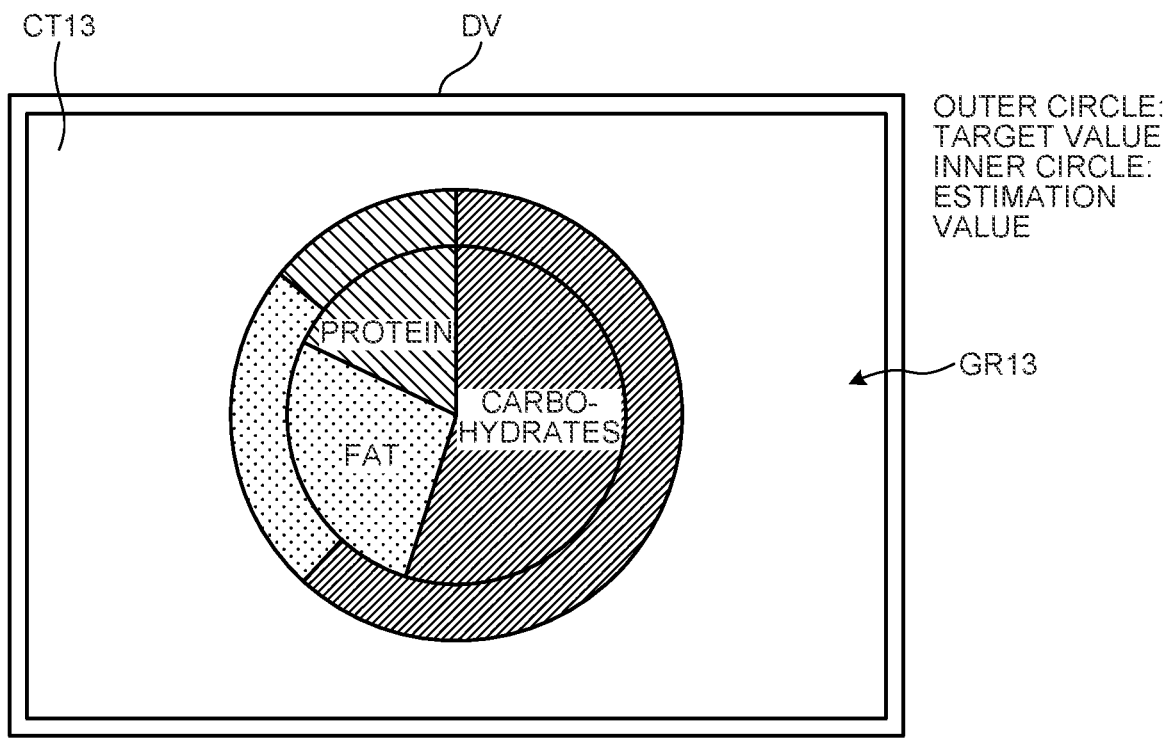
FIG. 19 is a diagram illustrating a modification of display of the nutrient intake balance.
Figure 20:
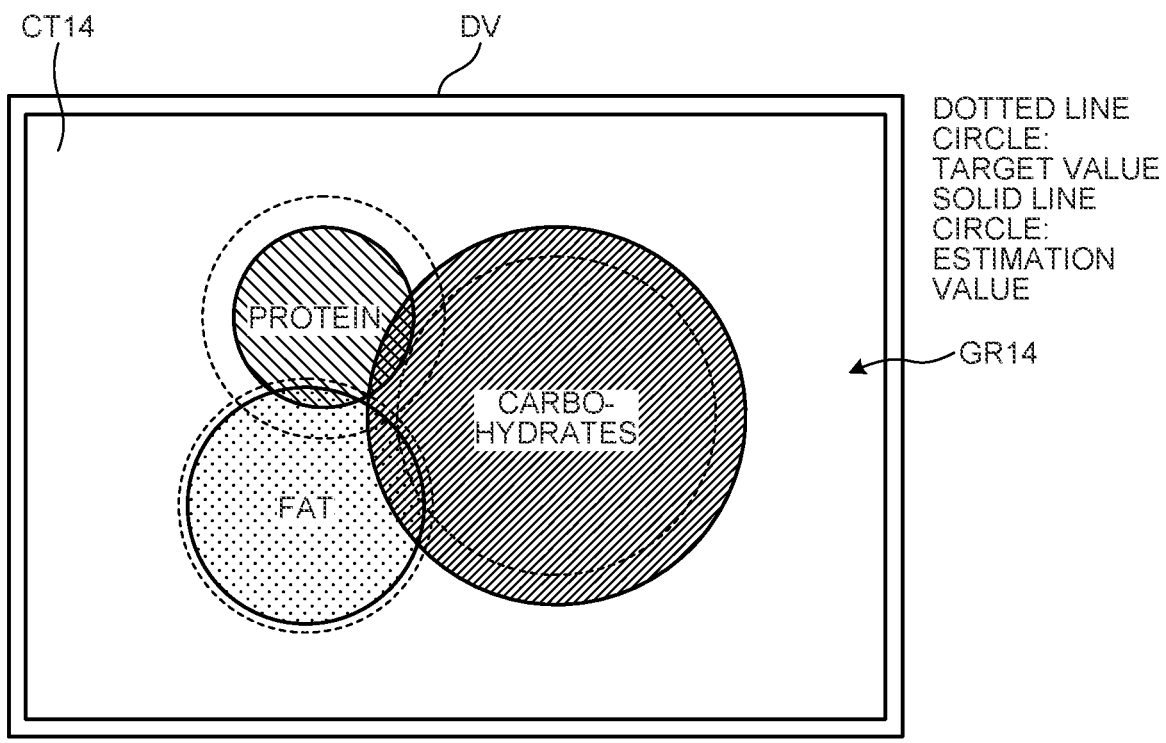
FIG. 20 is a diagram illustrating a modification of display of the nutrient intake balance.

First, the following describes an example of display using a graph other than the radar chart with reference to FIG. 17 to FIG. 20. FIG. 17 to FIG. 20 are diagrams illustrating modifications of display of the nutrient intake balance. Specifically, FIG. 17 is a diagram illustrating an example of display of the nutrient intake balance in a bar graph format. FIG. 18 is a diagram illustrating an example of display of the nutrient intake balance in a line graph format. FIG. 19 is a diagram illustrating an example of display of the nutrient intake balance in a pie graph format. FIG. 20 is a diagram illustrating an example of display of the nutrient intake balance in a bubble chart format. The nutrient intake amount output device DV illustrated in FIG. 17 to FIG. 20 may be the user terminal 10, or may be another device. FIG. 17 to FIG. 20 are different from the display example of the radar chart illustrated in FIG. 1 only in a display format, and the estimation processing is the same, so that description will be omitted as appropriate.

In the example of FIG. 17, the nutrient intake amount estimation device 100 generates content CT11 including a bar graph GR11. The nutrient intake amount estimation device 100 transmits the content CT11 to the nutrient intake amount output device DV. The nutrient intake amount output device DV that has received the content CT11 displays the content CT11. In the bar graph GR11, a back (left) side of each nutrient represents the target value, and a front (right) side thereof represents the estimation value. The bar graph GR11 indicates that the amount of carbohydrates is lower than the target amount, the amount of fat is close to the target amount, and the amount of protein is higher than the target amount.

In the example of FIG. 18, the nutrient intake amount estimation device 100 generates content CT12 including a line graph GR12. The nutrient intake amount estimation device 100 generates the content CT12 including the line graph GR12 by plotting the target value and the estimation value for each day of the week. The nutrient intake amount estimation device 100 transmits the content CT12 to the nutrient intake amount output device DV. The nutrient intake amount output device DV that has received the content CT12 displays the content CT12. In the line graph GR12, a dotted line of each nutrient represents the target value, and a solid line thereof represents the estimation value. The line graph GR12 indicates that the amount of fat is continuously lower than the target amount, and the amount of protein is continuously higher than the target amount.

In the example of FIG. 19, the nutrient intake amount estimation device 100 generates content CT13 including a pie graph GR13. The nutrient intake amount estimation device 100 transmits the content CT13 to the nutrient intake amount output device DV. The nutrient intake amount output device DV that has received the content CT13 displays the content CT13. In the pie graph GR13, an outer circle represents the target value, and an inner circle represents the estimation value. The pie graph GR13 indicates that the amount of carbohydrates is lower than the target amount, the amount of fat is close to the target amount, and the amount of protein is higher than the target amount.

In the example of FIG. 20, the nutrient intake amount estimation device 100 generates content CT14 including a bubble chart GR14. The nutrient intake amount estimation device 100 transmits the content CT14 to the nutrient intake amount output device DV. The nutrient intake amount output device DV that has received the content CT14 displays the content CT14. In the bubble chart GR14, among circles of the respective nutrients, a dotted line circle (a circle represented by a dotted line) represents the target value, and a solid line circle (a circle represented by a solid line) represents the estimation value. The bubble chart GR14 indicates that the amount of carbohydrates is higher than the target amount, the amount of fat is close to the target amount, and the amount of protein is lower than the target amount. The graphs illustrated in FIG. 17 to FIG. 20 are merely examples, and a graph in an optional format can be employed.

Figure 21:
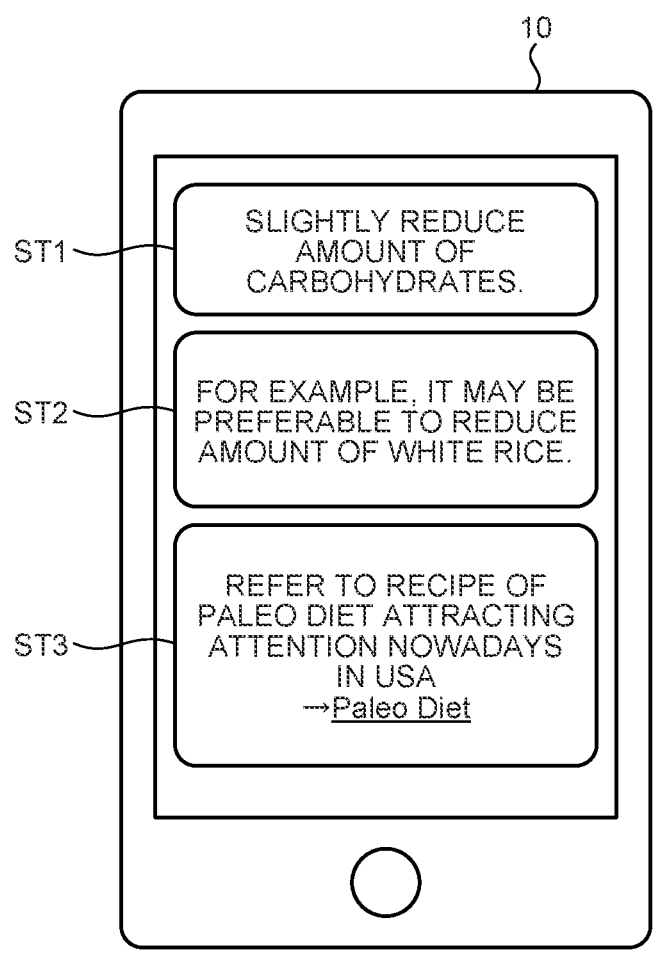
FIG. 21 is a diagram illustrating an example of recommendation based on estimation of the nutrient intake balance.

The information to be displayed based on the measurement result is not limited to the estimation result, and may be recommendation information related to nutrient intake of the user based on the estimation result. This point will be described below with reference to FIG. 21. FIG. 21 is a diagram illustrating an example of recommendation based on estimation of the nutrient intake balance. Similarly to FIG. 16, the following describes a display example in a case in which the estimation result is "excessive in carbohydrates" with reference to FIG. 21.

In the example of FIG. 21, the estimated nutrient intake balance of the user is "excessive in carbohydrates", and the user terminal 10 displays pieces of character information ST1 to ST3. Specifically, the user terminal 10 displays the character information ST1 as recommendation information for recommending the user to reduce the intake amount of carbohydrates. The user terminal 10 also displays the character information ST2 as recommendation information for recommending to reduce the intake amount of rice (white rice). The user terminal 10 also displays the character information ST3 as recommendation information for recommending to refer to a recipe of Paleo Diet. The character information ST3 includes a link written as "Paleo Diet", and in a case in which the user selects the link, the user terminal 10 displays content such as a Web page indicating the recipe of Paleo Diet.

The nutrient intake amount estimation device 100 determines to provide the pieces of character information ST1 to ST3 to the user based on the estimation result indicating that the estimated nutrient intake balance of the user is "excessive in carbohydrates". For example, the nutrient intake amount estimation device 100 may use a recommendation list as an at-a-glance list associating a plurality of pieces of the recommendation information such as the pieces of character information ST1 to ST3 with a tag indicating which nutrient balance corresponds to each piece of the recommendation information. In this case, the nutrient intake amount estimation device 100 may store the recommendation list in the storage part 120 (refer to FIG. 4), and select the recommendation information to be provided to the user from the recommendation list. For example, in a case in which the estimated nutrient intake balance of the user is "excessive in carbohydrates", the nutrient intake amount estimation device 100 selects the recommendation information associated with "excessive in carbohydrates" in the recommendation list as the recommendation information to be provided to the user.

The nutrient intake amount estimation device 100 may generate the recommendation information based on the estimation result. In the example of FIG. 21, the nutrient intake amount estimation device 100 may generate the pieces of character information ST1 to ST3 based on the estimation result indicating that the estimated nutrient intake balance of the user is "excessive in carbohydrates".

The nutrient intake amount estimation device 100 transmits the pieces of character information ST1 to ST3 to the user terminal 10. The user terminal 10 that has received the pieces of character information ST1 to ST3 displays the pieces of character information ST1 to ST3. In this way, the nutrient intake amount estimation system 1 displays the recommendation information based on a difference between the target nutrient intake amount and the estimated nutrient intake amount. The pieces of character information ST1 to ST3 illustrated in FIG. 21 are merely examples of the recommendation information. For example, in a case in which the intake amount of carbohydrates of the user is larger than the target intake amount, the nutrient intake amount estimation system 1 may notify the user that the intake of carbohydrates is excessive. In this case, the nutrient intake amount estimation system 1 may notify the user of the recommendation information for recommending to suppress the intake of carbohydrates because the intake amount of carbohydrates is excessive, such as "the amount of carbohydrates is excessive as compared with the target value". For example, the nutrient intake amount estimation device 100 generates character information ST4 including a description of "the amount of carbohydrates is excessive as compared with the target value", and transmits the character information ST4 to the user terminal 10. The user terminal 10 that has received the character information ST4 displays the character information ST4.

9. Estimation Model

The following describes the estimation model such as the models M1 to M9 described above.

9-1. Generation of Estimation Model

The estimation model such as the models M1 to M9 is generated by using learning data as a combination of the output value of the sensor device 50 and accuracy information (label) indicating which of the four balances including "well-balanced", "excessive in carbohydrates", "excessive in fat", and "excessive in protein" corresponds to the excretion smell corresponding to the output value. For example, the learning data includes a combination (also referred to as a "first combination") of the output value of the sensor device 50 that has detected the excretion smell of the user who had a well-balanced meal and the accuracy information (label) indicating that the output value corresponds to the well-balanced meal. For example, the learning data includes a combination (also referred to as a "second combination") of the output value of the sensor device 50 that has detected the excretion smell of the user who had a meal excessive in carbohydrates and the accuracy information (label) indicating that the output value corresponds to the meal excessive in carbohydrates. For example, the learning data includes a combination (also referred to as a "third combination") of the output value of the sensor device 50 that has detected the excretion smell of the user who had a meal excessive in fat and the accuracy information (label) indicating that the output value corresponds to the meal excessive in fat. For example, the learning data includes a combination (also referred to as a "fourth combination") of the output value of the sensor device 50 that has detected the excretion smell of the user who had a meal excessive in protein and the accuracy information (label) indicating that the output value corresponds to the meal excessive in protein.

The following describes a case in which the nutrient intake amount estimation device 100 generates the estimation model such as the models M1 to M9 as an example. The nutrient intake amount estimation device 100 generates the models M1 to M9 using the learning data including the first combination to the fourth combination. In a case in which the output value of each combination is input, the nutrient intake amount estimation device 100 compares classification information output from the estimation model itself such as the models M1 to M9 with the accuracy information indicating a classification corresponding to the output value while detecting an error, and repeatedly applies appropriate improvement so that the classification information can output the accuracy information to generate the models M1 to M9.

For example, the nutrient intake amount estimation device 100 performs learning processing so that, in a case in which the input value generated by using the output value of the first combination is input, the model M1 makes an output indicating "well-balanced" to generate the model M1. The nutrient intake amount estimation device 100 performs learning processing so that, in a case in which the input value generated by using the output value of the second combination is input, the model M1 makes an output indicating "excessive in carbohydrates" to generate the model M1. The nutrient intake amount estimation device 100 performs learning processing so that, in a case in which the input value generated by using the output value of the third combination is input, the model M1 makes an output indicating "excessive in fat" to generate the model M1. The nutrient intake amount estimation device 100 performs learning processing so that, in a case in which the input value generated by using the output value of the fourth combination is input, the model M1 makes an output indicating "excessive in protein" to generate the model M1. The nutrient intake amount estimation device 100 also generates the models M2 to M9 by the same learning processing. The processing described above is merely an example, and the nutrient intake amount estimation device 100 may generate the models M1 to M9 by appropriately using various learning methods.

For example, the generation part 133 of the nutrient intake amount estimation device 100 generates the estimation model such as the models M1 to M9 by the processing described above. Alternatively, the estimation model such as the models M1 to M9 may be generated by a device (model generating device) other than the nutrient intake amount estimation device 100, and the nutrient intake amount estimation device 100 may acquire (receive) the estimation model such as the models M1 to M9 from the model generating device.

9-2. Output Example of Estimation Model

The example described above exemplifies the case in which the estimation model such as the models M1 to M9 outputs the information indicating any of the four balances including "well-balanced", "excessive in carbohydrates", "excessive in fat", and "excessive in protein", but the estimation model is not limited to the model (classifier) for classifying the four balances including "well-balanced", "excessive in carbohydrates", "excessive in fat", and "excessive in protein". The following exemplifies this point.

9-2-1. Five or More Classifications

For example, the estimation model may be a classifier for making five or more classifications. For example, the estimation model may be a classifier for making seven classifications including "well-balanced", "excessive in carbohydrates", "excessive in fat", "excessive in protein", "deficient in carbohydrates", "deficient in fat", and "deficient in protein".

For example, the estimation model may be a classifier that can classify a degree of excess into a plurality of stages. For example, the estimation model may be a classifier that classifies an excess of each nutrient into two stages including a normal excess and a large excess larger than the normal excess. For example, the estimation model may be a classifier that makes seven classifications including "well-balanced", "excessive in carbohydrates", "largely excessive in carbohydrates", "excessive in fat", "largely excessive in fat", "excessive in protein", and "largely excessive in protein".

The processing for generating the model is the same as the learning processing by using the learning data described above, so that description thereof will not be repeated. The nutrient intake amount estimation system 1 may perform estimation processing by using the estimation model that makes five or more classifications as described above to monitor the nutrient balance of the user.

9-2-2. Estimation of Ratio

For example, the estimation model may be a model (ratio output model) that outputs a value (score) indicating a ratio of a nutrient as an estimation target. For example, the estimation model may be a ratio output model that outputs, based on the output value of the sensor device 50 that has detected the excretion smell, scores indicating ratios of at least two nutrients among carbohydrates, fat, protein, vitamins, and minerals of the taken nutrients corresponding to the excretion smell. For example, the model M1 as a neural network may be a ratio output model that outputs a value (score) indicating a ratio of each nutrient.

For example, the nutrient intake amount estimation device 100 generates the model M1 as the ratio output model by using combination learning data of the accuracy information (label) indicating the ratios of nutrients of each meal and the output value of the sensor device 50 that has detected the excretion smell of the user who has taken the meal. The nutrient intake amount estimation device 100 generates the model M1 as the ratio output model to output, in a case in which the input value generated by using the output value of each combination is input, the ratio of the nutrient of the meal corresponding to the output value. The nutrient intake amount estimation device 100 may calculate the estimation value of each nutrient illustrated in the content CT1 of FIG. 2 by using the model M1 as the ratio output model, and generate the radar chart RC1 including the estimation chart ES1.

9-2-3. Estimation of Amount

For example, the estimation model may be a model (amount output model) that outputs a value (score) indicating the intake amount of the nutrient as an estimation target. For example, the estimation model may be an amount output model that outputs, based on the output value of the sensor device 50 that has detected the excretion smell, scores indicating intake amounts of at least two nutrients among carbohydrates, fat, protein, vitamins, and minerals of the taken nutrients corresponding to the excretion smell.

For example, the nutrient intake amount estimation device 100 generates the amount output model by using the combination learning data of the accuracy information (label) indicating the amount of nutrients of each meal and the output value of the sensor device 50 that has detected the excretion smell of the user who has taken the meal. The nutrient intake amount estimation device 100 generates the amount output model to output, in a case in which the input value generated by using the output value of each combination is input, the intake amount of nutrients of a meal corresponding to the output value.

When the nutrient intake amount estimation device 100 estimates the intake amount of each nutrient of the user by using the amount output model, the nutrient balance of the user can be monitored considering not only a relation between the nutrients but also a concept of the amount of each nutrient. For example, the nutrient intake amount estimation device 100 stores, in the storage part 120, the target nutrient intake amount that is the nutrient intake amount aimed at by the user. The nutrient intake amount estimation device 100 then transmits, to the user terminal 10, information indicating the amount of nutrients estimated to be taken by the user (estimated nutrient intake amount) and the target nutrient intake amount. The user terminal 10 displays the received information indicating the estimated nutrient intake amount and the target nutrient intake amount. For example, the user terminal 10 may calculate a difference between the received estimated nutrient intake amount and target nutrient intake amount, and display the difference. The nutrient intake amount estimation system 1 may estimate the intake amount of a specific nutrient (specific nutrient), and output information indicating the estimated nutrient intake amount that has been estimated and the target nutrient intake amount of the specific nutrient. For example, the nutrient intake amount estimation system 1 may perform the output processing described above assuming a nutrient designated by the user as the specific nutrient.

The nutrient intake amount estimation device 100 may estimate the intake amount of each nutrient by using the amount output model, and calculate the ratio of each nutrient by using the estimated intake amount of each nutrient. The nutrient intake amount estimation device 100 may use the ratio of each nutrient that is calculated from the intake amount of each nutrient to perform the processing by using the ratio described above.

10. Nutrient Intake Amount Output Device

The example described above exemplifies the user terminal 10 used by the user as an example of the nutrient intake amount output device, but the nutrient intake amount output device is not limited to the user terminal 10 but may be any device that can make a desired output. For example, in a case of displaying the nutrient intake balance as in the example of FIG. 2, any device having a display function may be used. For example, the nutrient intake amount output device may be a terminal device disposed in the toilet space PS1 such as the toilet operation device or a mirror disposed in the toilet space PS1. The nutrient intake amount output device may be a terminal device such as a smartphone or a tablet terminal used by health professionals.

For example, the nutrient intake amount estimation device 100 is connected to the toilet operation device, the terminal device disposed in the toilet space PS1, or the terminal device used by health professionals via the predetermined network N (refer to FIG. 3) in a wired or wireless manner, and can transmit/receive information thereto/therefrom. The nutrient intake amount estimation device 100 transmits the estimated nutrient balance of the user to the toilet operation device, the terminal device disposed in the toilet space PS1, or the terminal device used by health professionals.

11. Authentication

In the example of FIG. 1, personal authentication is performed by using the toilet operation device disposed in the toilet space PS1. In this case, the toilet operation device disposed in the toilet space PS1 functions as an authentication unit. For example, the toilet operation device can designate the user, and functions as an authentication device with which the user performs personal authentication by operating the toilet operation device and designating the user. In the example of FIG. 1, the user U1 performs personal authentication by operating the toilet operation device and designating the user U1.

In a case in which the toilet operation device is a terminal device such as a tablet terminal including a display screen, the user performs personal authentication by designating the user in a user group displayed on the toilet operation device.

In a case in which the user carries the user terminal 10 into the toilet space, the user terminal 10 may communicate with the toilet operation device to cause the toilet operation device to specify the user using the user terminal 10 as the user who uses the toilet space. In the example of FIG. 1, the user terminal 10 of the user U1 is paired with the toilet operation device by Bluetooth and the like, for example, to specify the user U1 to be the user who uses the toilet space PS1.

Alternatively, personal authentication may be performed based on detection results of various sensors disposed in the toilet space PS1. In this case, the nutrient intake amount estimation device 100 is an authentication device including an authentication part that specifies the user based on the detection results of various sensors of the sensor device 50. The authentication part of the nutrient intake amount estimation device 100 functions as an authentication unit. For example, the nutrient intake amount estimation device 100 specifies the user based on the detection result of the sensor such as the sensor device 50. The nutrient intake amount estimation device 100 may use a detection result of any sensor with which personal authentication (specification) of the user can be performed.

The nutrient intake amount estimation device 100 communicates with a sensor device such as the sensor device 50, receives information detected by the sensor device from the sensor device, and specifies the user based on the information. For example, the nutrient intake amount estimation device 100 may specify the user by using detection information (an image and the like) obtained by the sensor device including an image sensor for photographing an entrance of the toilet space PS1. In this case, the nutrient intake amount estimation device 100 may specify the user who uses the toilet space PS1 by comparing an image detected by the image sensor with an image of each user stored in the storage part 120.

The processing described above is merely an example, and personal authentication may be performed by any processing capable of performing specification (personal authentication) of the user of the toilet space.

12. Toilet Space

The toilet space in which the sensor device 50 is disposed is not limited to the toilet space PS1 of the house as illustrated in FIG. 1, but may be a toilet space in a facility other than the house. As described above, in a case in which specification (personal authentication) of the user of the toilet space can be performed, the toilet space in which the sensor device 50 is disposed may be a toilet space provided at any place. For example, the toilet space in which the sensor device 50 is disposed may be a toilet space in a shop such as a department store, an amusement park, a sports arena, an office building, a park, a parking lot, and the like.

Additional effects and modifications can be easily conceived by those skilled in the art. Thus, a broader aspect of the present invention is not limited to the specific details and the typical embodiment that are represented and described above. Accordingly, the present invention can be variously modified without departing from the spirit or scope of the comprehensive concept of the invention as defined by accompanying claims and equivalents thereof.

REFERENCE SIGNS LIST

1 NUTRIENT INTAKE AMOUNT ESTIMATION SYSTEM
100 NUTRIENT INTAKE AMOUNT ESTIMATION DEVICE
110 COMMUNICATION PART
120 STORAGE PART
121 NUTRIENT INTAKE TARGET BALANCE INFORMATION STORAGE PART
122 MODEL INFORMATION STORAGE PART
123 USER INFORMATION STORAGE PART
130 CONTROL PART
131 ACQUISITION PART
132 ESTIMATION PART
133 GENERATION PART
134 TRANSMISSION PART
10 USER TERMINAL (NUTRIENT INTAKE AMOUNT OUTPUT DEVICE)
11 COMMUNICATION PART
12 INPUT PART
13 DISPLAY PART (OUTPUT PART)
14 STORAGE PART
15 CONTROL PART
151 ACQUISITION PART
152 DISPLAY CONTROL PART
153 RECEPTION PART
154 TRANSMISSION PART
16 VOICE OUTPUT PART
PS1 TOILET SPACE

What is claimed is:

1. A nutrient intake amount estimation system comprising:
   a sensor that is disposed in a toilet space, and configured to detect an excretion smell related to excretion of a user of the toilet space;
   an estimation unit configured to estimate, in accordance with an input based on an output value of the sensor, an estimated nutrient intake amount that is an amount of nutrients taken by the user by using an estimation model configured to indicate a correlation between an amount of nutrients not consumed by the user and the output value of the sensor; and
   an output unit configured to output information based on the estimated nutrient intake amount.

2. The nutrient intake amount estimation system according to claim 1, further comprising:
   a storage unit configured to store a target nutrient intake amount that is a nutrient intake amount aimed at by the user, wherein
   the output unit outputs the target nutrient intake amount and the estimated nutrient intake amount.

3. The nutrient intake amount estimation system according to claim 1, further comprising:
   a storage unit configured to store a target nutrient intake amount that is a nutrient intake amount aimed at by the user, wherein
   the output unit outputs a difference between the target nutrient intake amount and the estimated nutrient intake amount.

4. The nutrient intake amount estimation system according to claim 3, wherein the output unit displays recommendation information based on a difference between the target nutrient intake amount and the estimated nutrient intake amount.

5. The nutrient intake amount estimation system according to claim 2, wherein the target nutrient intake amount stored in the storage unit is set based on selection by the user or information related to the user.

6. The nutrient intake amount estimation system according to claim 1, wherein
   the estimation unit estimates an estimated nutrient intake balance that is a balance of nutrients taken by the user as the estimated nutrient intake amount; and
   the output unit outputs information based on the estimated nutrient intake balance.

7. The nutrient intake amount estimation system according to claim 1, wherein
   the estimation unit estimates an estimated specific nutrient intake amount that is an amount of a specific nutrient taken by the user as the estimated nutrient intake amount; and
   the output unit outputs information based on the estimated specific nutrient intake amount.

8. The nutrient intake amount estimation system according to claim 6, wherein the output unit displays a balance of at least two nutrients selected from carbohydrates, fat, protein, vitamins, and minerals as a graph.

9. The nutrient intake amount estimation system according to claim 1, wherein the sensor is disposed on a toilet seat or a closet bowl in the toilet space.

10. The nutrient intake amount estimation system according to claim 1, wherein
the estimation unit is connected to the output unit in a communicable manner via an electric communication line, and
information is transmitted from the estimation unit to the output unit via the electric communication line.

11. The nutrient intake amount estimation system according to claim 1, further comprising:
an authentication unit configured to authenticate the user.

12. The nutrient intake amount estimation system according to claim 1, further comprising:
a transmission unit configured to transmit data of the estimated nutrient intake amount to a terminal device via an electric communication line.

13. The nutrient intake amount estimation system according to claim 1, wherein the excretion smell contains a smell of at least one of feces, urine, and gas excreted by the user.

14. A nutrient intake amount estimation device comprising:
an acquisition part configured to acquire an output value that is output by a sensor disposed in a toilet space after detecting an excretion smell related to excretion of a user of the toilet space; and
an estimation part configured to estimate, in accordance with an input based on an output value of the sensor, an estimated nutrient intake amount that is an amount of nutrients taken by the user by using an estimation model configured to indicate a correlation between an amount of nutrients not consumed by the user and the output value of the sensor.

15. A nutrient intake amount estimation system comprising:
a sensor that is disposed in a toilet space, and configured to detect an excretion smell related to excretion of a user of the toilet space;
an estimation unit configured to estimate, in accordance with an input based on an output value of the sensor, an estimated nutrient intake amount that is an amount of nutrients taken by the user by using an estimation model configured to indicate a correlation between an amount of nutrients not consumed by the user and the output value of the sensor.

* * * * *